US010646697B2

(12) United States Patent
Gotou et al.

(10) Patent No.: US 10,646,697 B2
(45) Date of Patent: May 12, 2020

(54) BALLOON COATING METHOD, BALLOON ROTATING METHOD AND BALLOON COATING APPARATUS

(71) Applicant: TERUMO KABUSHIKI KAISHA, Shibuya-ku, Tokyo (JP)

(72) Inventors: Hiroshi Gotou, Kanagawa (JP); Yasuo Kurosaki, Kanagawa (JP); Eisuke Furuichi, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 446 days.

(21) Appl. No.: 15/136,269

(22) Filed: Apr. 22, 2016

(65) Prior Publication Data

US 2016/0310708 A1    Oct. 27, 2016

(30) Foreign Application Priority Data

Apr. 23, 2015    (JP) ................. 2015-088384

(51) Int. Cl.
    A61M 25/10    (2013.01)
    B05C 13/02    (2006.01)
    B05C 5/02     (2006.01)
    B05D 1/26     (2006.01)
    B05D 1/00     (2006.01)

(52) U.S. Cl.
    CPC ....... *A61M 25/1029* (2013.01); *B05C 5/0216* (2013.01); *B05C 13/025* (2013.01); *A61M 2025/1031* (2013.01); *B05C 5/0208* (2013.01); *B05D 1/002* (2013.01); *B05D 1/26* (2013.01)

(58) Field of Classification Search
    CPC ...... A61M 25/1029; A61M 2025/1031; B05C 5/0216; B05C 5/0208; B05C 13/025; B05D 1/002; B05D 1/26
    See application file for complete search history.

(56) References Cited

U.S. PATENT DOCUMENTS

| 8,597,720 B2 | 12/2013 | Hoffmann et al. |
| 2010/0040766 A1 | 2/2010 | Chappa et al. |
| 2011/0295200 A1* | 12/2011 | Speck ............ A61L 29/06 |
| | | 604/103.02 |

FOREIGN PATENT DOCUMENTS

| JP | 2015-009095 A | 1/2015 |
| WO | 2013/181498 A1 | 12/2013 |

OTHER PUBLICATIONS

An English Translation of the Office Action (Notice of Reasons for Refusal) dated Dec. 23, 2019, by the Japanese Patent Office in corresponding Japanese Patent Application No. 2016-086015. (5 pages).

* cited by examiner

*Primary Examiner* — Dah-Wei D. Yuan
*Assistant Examiner* — Andrew J Bowman
(74) *Attorney, Agent, or Firm* — Buchanan Ingersoll & Rooney PC

(57) ABSTRACT

A balloon coating method for forming a coating layer containing a water-insoluble drug on the outer surface of a balloon of a balloon catheter, wherein the balloon catheter includes an elongate shaft possessing a distal portion at which is provided the balloon which is inflatable. The balloon coating method includes: holding the shaft on a support part capable of rotating about an axis of the balloon; and moving a dispensing tube for supplying a coating liquid containing the drug relative to the balloon in an axial direction of the balloon, while rotating the balloon together with the support part, thereby to coat the outer surface of the balloon with the coating liquid.

20 Claims, 11 Drawing Sheets

BALLOON COATING METHOD, BALLOON ROTATING METHOD AND BALLOON COATING APPARATUS

CROSS-REFERENCES TO RELATED APPLICATIONS

This application claims priority to Japanese Application No. 2015-088384 filed on Apr. 23, 2015, the entire content of which is incorporated herein by reference.

TECHNICAL FIELD

The present disclosure relates to a balloon coating method, a balloon rotating method and a balloon coating apparatus for forming a coating layer containing a drug on a surface of a balloon.

BACKGROUND DISCUSSION

In recent years, balloon catheters have been used for improving lesion affected areas (stenosed parts) in body lumens. A balloon catheter normally includes an elongate shaft portion, and a balloon which is provided on the distal side of the shaft portion and is inflatable in the radial direction. After the balloon in a deflated state is brought to a target site in the body by way of a small body lumen, the balloon is inflated, whereby the lesion affected area can be pushed wide open.

If a lesion affected area is forcibly pushed wide open, however, excessive proliferation of smooth muscle cells may occur, causing new stenosis (restenosis). In view of this, recently, drug eluting balloons (DEBs) wherein an outer surface of a balloon is coated with a drug for restraining stenosis have been used. The drug eluting balloon, by being inflated, is able to instantaneously release the drug contained in the coating on the outer surface of the balloon to the lesion affected area and transfer the drug to the living body tissue, thereby restraining restenosis.

In recent years, it has been becoming clear that the morphological form of the drug in the coating on the balloon surface influences the releasing property of the drug from the balloon surface and/or the transferability of the drug to the tissue at the lesion affected area. For this reason, it is said that it is important to control the crystalline form or amorphous form of the drug.

A variety of methods have been proposed for coating a balloon with a drug. For instance, U.S. Pat. No. 8,597,720 discloses a method in which a coating solution containing a drug (therapeutic agent) is supplied to a surface of a balloon while the balloon is being rotated, and the coating liquid is dried to form a coating layer containing the drug.

SUMMARY

The drug in the coating on the outer surface of the balloon can assume different morphological forms such as crystalline form, amorphous form and mixed forms thereof, depending on various conditions such as the length of time of volatilization of the solvent. Neither of the crystalline form and the amorphous form is more desirable than the other, and it is desirable that the morphological form of the drug can be selected according to the purpose.

There is a need for a balloon coating method, a balloon rotating method and a balloon coating apparatus by which a coating liquid can be applied to an outer surface of a balloon in an appropriate quantity, and the morphological form of the drug in the coating formed on the balloon can be set appropriately.

One aspect of the present disclosure involves a balloon coating method for forming a coating layer containing a water-insoluble drug on the outer surface of a balloon of a balloon catheter, wherein the balloon catheter includes an elongate shaft possessing a distal portion at which is located the balloon which is inflatable The method includes: holding the shaft on a support part configured to rotate about an axis of the balloon; and moving a dispensing tube relative to the balloon in an axial direction of the balloon while rotating the balloon together with the support part about the axis of the balloon and while also dispensing the coating liquid containing the water-insoluble drug from the dispensing tube to coat the outer surface of the balloon with the coating liquid.

According to the balloon coating method implemented as above, the balloon is rotated with the shaft held on the rotatable support part. Therefore, a bend or the like of the shaft is less liable to influence the rotation of the balloon, so that the balloon is less liable to be twisted or get eccentric. For this reason, the position of the outer surface of the balloon is not liable to fluctuate during rotation, and the coating liquid can be applied to the outer surface of the balloon in an appropriate quantity. In addition, since the position of the outer surface of the balloon is not liable to fluctuate during rotation, the contact force in contact of the dispensing tube with the balloon can be easily set to a desirable value, so that, for example, the morphological form of the drug in the coating formed on the balloon can be set appropriately.

The balloon coating method may be implemented such that the support part includes a support base formed with a rectilinear groove in which at least part of the shaft can be accommodated, and a lid configured to cover at least part of the groove, and, in the holding of the shaft, the shaft is accommodated in the groove and the groove is covered with the lid, whereby the shaft is held between the support base and the lid. By virtue of this, the shaft can be held easily and reliably in such a manner as not to slip out of the groove.

The balloon coating method may be implemented so that the holding of the shaft involves the shaft being clamped by the support base and the lid. In this case, the shaft can be firmly held on the support part, and rotation of the balloon is stabilized. As a result, the balloon is less liable to be twisted or become eccentric, and the position of the outer surface of the balloon is less liable to fluctuate during rotation.

The holding of the shaft can include holding the shaft on the support part, with a core member positioned in the shaft. According to this, deformation of the shaft can be restrained, even when the shaft is held on the support part.

The coating of the balloon may involve the balloon catheter being rotatably supported by a bearing section provided on a distal side of a rotation driving section configured to apply a rotating force to the support part, while rotating the balloon catheter by the rotation driving section. The rotation of the support part extending distally from the rotation driving section is stabilized. Therefore, the rotation of the balloon is stabilized, and the balloon becomes less liable to be twisted or get eccentric.

According to another aspect of the present disclosure, a balloon rotating method for rotating a balloon catheter provided with an inflatable balloon at a distal portion of an elongate shaft includes: holding the shaft on a support part configured to rotate about an axis of the balloon; and rotating the balloon together with the support part.

The balloon rotating method may be implemented so that the balloon is rotated with the shaft held on the rotatable support part. Therefore, bending or the like of the shaft is not liable to influence the rotation of the balloon, so that the balloon is not liable to be twisted or become eccentric. Consequently, the position of an outer surface of the balloon is not liable to fluctuate during rotation.

The balloon rotating method may be implemented such that the support part includes a support base formed with a rectilinear groove in which at least part of the shaft is accommodated, and a lid configured to cover at least part of the groove, and, in the holding of the shaft, the shaft is accommodated in the groove and the groove is covered with the lid, whereby the shaft is held on the support base. In this case, the shaft can be held easily and reliably in such a manner as not to slip off from the groove.

The holding of the shaft may include the shaft being clamped by the support base and the lid. According to this, the shaft can be firmly held on the support part, and the rotation of the balloon is stabilized. Consequently, the balloon is less liable to be twisted or become eccentric, and the position of the outer surface of the balloon is less liable to fluctuate during rotation.

The holding of the shaft may involve holding the shaft on the support part, with a core member inserted in the shaft. This helps ensure that deformation of the shaft can be restrained, even when the shaft is held on the support part.

The coating of the balloon may include the balloon catheter being rotatably supported by a bearing section provided on a distal side of a rotation driving section configured to apply a rotating force to the support part, while rotating the balloon catheter by the rotation driving section. By virtue of this, the rotation of the support part extending distally from the rotation driving section is stabilized, and the rotation of the balloon becomes stable. As a result, the balloon is less liable to be twisted or become eccentric, and the position of the outer surface of the balloon is less liable to fluctuate during rotation.

According to a further aspect of the present disclosure, a balloon coating apparatus is configured to form a coating layer containing a water-insoluble drug on the outer surface of a balloon of a balloon catheter, wherein the balloon catheter includes an elongate shaft possessing a distal portion at which is located the balloon which is inflatable. The apparatus includes: a support part rotatable about an axis of the balloon while holding the shaft; a rotation driving section configured to rotate the support part; and a coating section that moves a dispensing tube for supplying a coating liquid containing the drug relative to the balloon in an axial direction of the balloon, to thereby coat the outer surface of the balloon with the coating liquid.

According to the balloon coating apparatus configured as above, the balloon can be rotated while the shaft is held on the rotatable support part. Therefore, a bend or the like of the shaft is not liable to influence the rotation of the balloon, so that the balloon is not liable to be twisted or become eccentric. Therefore, the position of the outer surface of the balloon is less liable to fluctuate during rotation, and the coating liquid can be applied to the outer surface of the balloon in an appropriate quantity. In addition, since the position of the outer surface of the balloon is not liable to fluctuate during rotation, the contact force in contact of the dispensing tube with the balloon can be easily set to a desirable value, so that, for example, the morphological form of the drug in the coating formed on the balloon can be set appropriately.

In the balloon coating apparatus, the support part may include a support base formed with a rectilinear groove in which at least part of the shaft can be accommodated, and a lid configured to cover at least part of the groove. In this case, by accommodating the shaft in the groove and covering the groove with the lid, the shaft can be held easily and reliably in such a manner as not to slip off from the groove.

The balloon coating apparatus may have a configuration in which the support base and the lid clamp the shaft therebetween. According to this configuration, the shaft can be firmly held on the support part, and the rotation of the balloon is stabilized. Therefore, the balloon is less liable to be twisted or become eccentric, and the position of the outer surface of the balloon is less liable to fluctuate during rotation.

The balloon coating apparatus may further include a bearing section configured to support the support part on a distal side of the rotation driving section in such a manner that the support part can be rotated. In this case, the rotation of the support part extending distally from the rotation driving section is stabilized, so that the rotation of the balloon is stabilized. For this reason, the balloon is less liable to be twisted or become eccentric, and the position of the outer surface of the balloon is less liable to fluctuate during rotation.

BRIEF DESCRIPTION OF THE DRAWINGS

FIGS. 4A and 4B are plan views showing a driving shaft, wherein FIG. 4A depicts a state before the driving shaft is interlocked to a three-way cock, and FIG. 4B depicts a state after the driving shaft is interlocked to the three-way cock.

DETAILED DESCRIPTION

Figure 1:
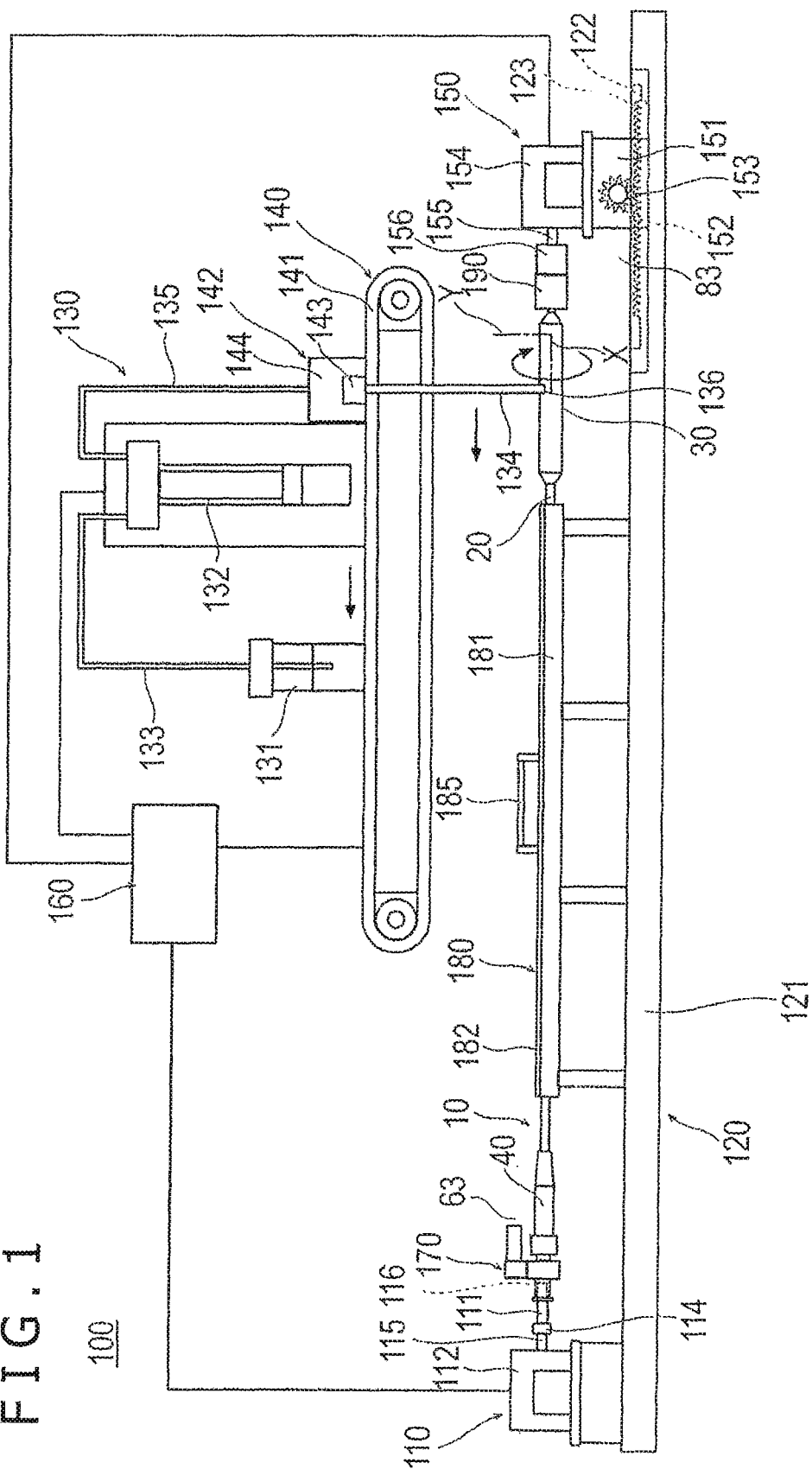
FIG. 1 is a schematic view showing an apparatus configured to carry out a balloon coating method according to a first embodiment of the present disclosure.

Set forth below, with reference to the accompanying drawing figures, is a detailed description of embodiments of a balloon coating method and a balloon rotating method for forming a drug-containing coating layer on a balloon surface representing examples of the inventive balloon coating method and balloon rotating method disclosed here. Dimensional ratios in the drawings may be exaggerated for convenience of explanation and may therefore be different from the actual ratios.

<First Embodiment>

A balloon coating method according to a first embodiment of the present disclosure is a method of forming a coating layer containing a water-insoluble drug on a surface of a balloon, and is carried out by a balloon coating apparatus 100 illustrated in FIG. 1. In the description below, the end of a balloon catheter 10 that is inserted into a body lumen will be referred to as the "distal end" or "distal side," and the end at which the operator's hand operation occurs will be referred to as the "proximal end" or "proximal side."

Figure 2:
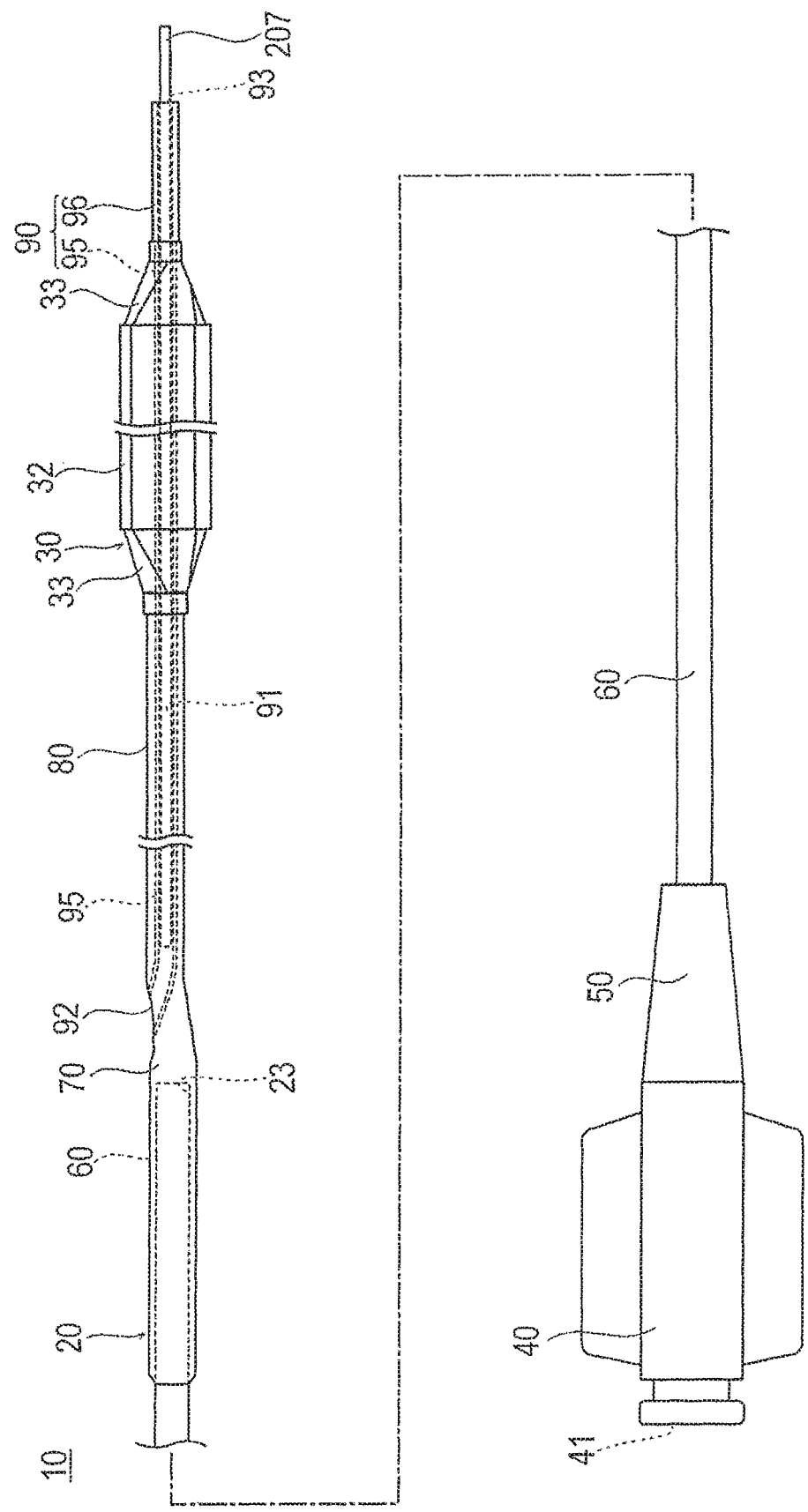
FIG. 2 is a plan view showing a balloon catheter.
Figure 3:
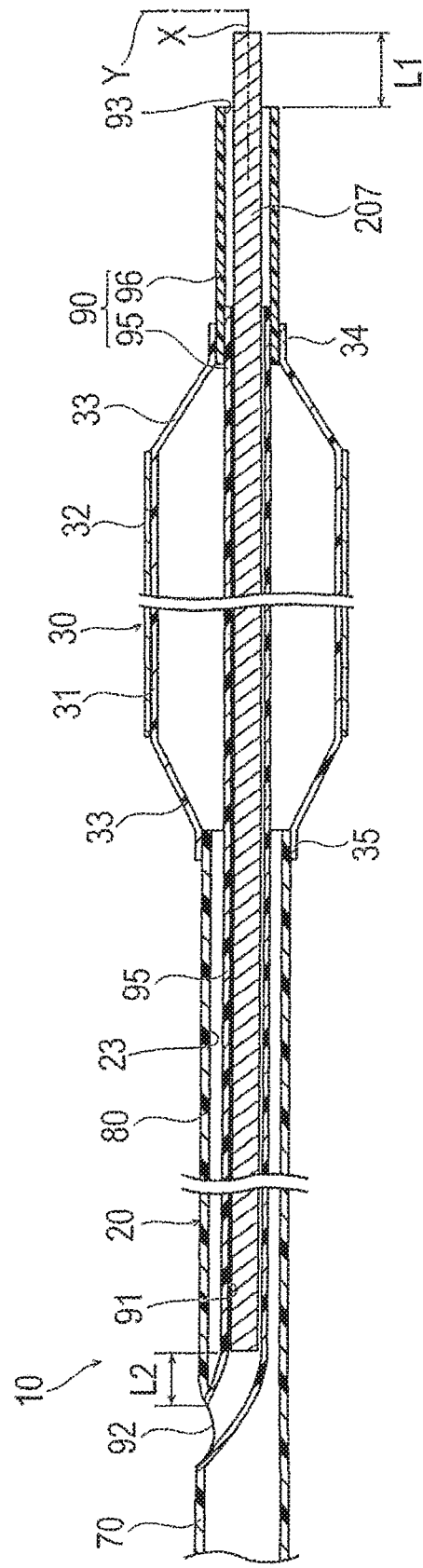
FIG. 3 is a cross-sectional view showing a distal portion of the balloon catheter.

First of all, the structure of the balloon catheter 10 will be described. The balloon catheter 10 is a so-called rapid exchange type catheter. As illustrated in FIGS. 2 and 3, the balloon catheter 10 includes an elongate catheter shaft 20 (shaft), a balloon 30 provided on a distal portion of the catheter shaft 20, a hub 40 firmly attached (fixed) to a proximal end of the catheter shaft 20, and an anti-kinking tube 50 provided at a joint portion between the catheter shaft 20 and the hub 40.

The catheter shaft 20 includes a tube-shaped (tubular) proximal shaft 60 whose proximal end is firmly attached (fixed) to the hub 40, a tube-shaped (tubular) intermediate shaft 70 covering a distal side or distal end of the proximal shaft 60, a tube-shaped (tubular) distal shaft 80 provided on the distal side of the intermediate shaft 70, and a tube-shaped (tubular) inner tube 90 disposed inside the distal shaft 80. Inside the proximal shaft 60, the intermediate shaft 70 and the distal shaft 80 is an inflation lumen 23 through which an inflation fluid for inflating the balloon 30 flows.

The inner tube 90 includes an inner tube shaft 95 which penetrates the inside of the distal shaft 80 and the balloon 30 in a coaxial manner, and a flexible tip 96 interlocked to a distal portion of the inner tube shaft 95. The tip 96 extends distally beyond the distal end of the balloon 30, and a distal portion of the balloon 30 is joined to an outer circumferential surface of a proximal portion of the tip 96 in a liquid-tight/fluid-tight manner. On the other hand, the proximal end of the inner tube shaft 95 is firmly attached (fixed) to a part in the outer circumferential direction of the intermediate shaft 70 (a side opening formed in a side surface) in a liquid-tight/fluid-tight manner, and a proximal opening of the inner tube shaft 95 is exposed to the outside of the intermediate shaft 70, thereby constituting a proximal opening portion 92. An inside space ranging from the distal end of the inner tube 90 to the proximal opening portion 92 constitutes a guide wire lumen 91. A guide wire is inserted in and passed through the inner tube 90, while a distal opening portion 93 of the tip 96 constituting the inner tube 90 serves as an entrance, whereas the proximal opening portion 92 of the inner shaft 95 constituting the inner tube 90 serves as an exit. The proximal opening portion 92 may be provided in the proximal shaft 60 or the distal shaft 80, instead of the intermediate shaft 70, or may be provided at a boundary portion between the intermediate shaft 70 and the distal shaft 80.

The materials constituting the distal shaft 80, the inner tube shaft 95, the tip 96 and the intermediate shaft 70 are not particularly limited. Examples of the materials which can be preferably used include polymeric materials such as polyolefins (e.g., polyethylene, polypropylene, polybutene, ethylene-propylene copolymer, ethylene-vinyl acetate copolymer, ionomer, or mixtures of two or more of them), crosslinked polyolefins, polyvinyl chloride, polyamides, polyamide elastomers, polyesters, polyester elastomers, polyurethanes, polyurethane elastomers, fluororesins, polyimides, and mixtures thereof.

The material constituting the proximal shaft 60 is preferably a material which is comparatively high in rigidity. Examples of the material which can be preferably used include metals such as Ni—Ti alloys, brass, steel special use stainless (SUS), aluminum, etc. and resins such as polyimides, vinyl chloride, polycarbonate, etc.

The hub 40 is provided with a hub proximal opening portion 41 that communicates with the inflation lumen 23 of the catheter shaft 20 and functions as a port through which the inflation fluid flows in and out. The hub 40 is fixed in a liquid-tight/fluid-tight connection with the proximal shaft 60.

The anti-kinking tube 50 is disposed outside of the proximal shaft 60, in order to prevent the proximal shaft 60 from kinking near the distal end of the hub 40.

The balloon 30 is for pushing open (outwardly expanding) a stenosed part by being inflated. At a central portion in the axial direction X of the balloon 30, there is formed a cylindrical portion 31 having a cylindrical shape with a constant outside diameter when inflated. On both sides of the cylindrical portion 31 in the axial direction X, there are formed tapered portions 33 at which the outside diameter gradually varies. The cylindrical portion 31 and the tapered portions 33 on both sides constitute a region in which the balloon 30 is actually inflated. A coating layer 32 containing a drug is formed on the whole part of an outside surface of the cylindrical portion 31. The range of the balloon 30 where the coating layer 32 is formed is not limited only to the cylindrical portion 31 but may include at least part of the tapered portions 33 in addition to the cylindrical portion 31; alternatively, the coating layer 32 may be formed on only part of the cylindrical portion 31.

A portion of the balloon 30 on the distal side of the distal-side tapered portion 33 constitutes a distal joint portion 34 (distal joint portion or distal joined region) that is joined, by adhesion or fusion bonding, to an outer circumferential surface of the tip 96 constituting the inner tube 90, in a liquid-tight/fluid-tight manner. A portion of the balloon 30 on the proximal side of the proximal-side tapered portion 33 constitutes a proximal joint portion 35 (proximal joined region) that is joined, by adhesion or fusion bonding, to an outer circumferential surface of a distal portion of the distal shaft 80 in a liquid-tight/fluid-tight manner. The inside of the balloon 30 communicates with the inflation lumen 23 formed in the catheter shaft 20, and the inflation fluid can flow into the balloon 30 from the proximal side through the inflation lumen 23. The balloon 30 is inflated when the inflation fluid flows into the balloon 30, and is brought into a folded state when the inflation fluid having flowed into the balloon is subsequently discharged from the balloon. The part to which a distal portion of the balloon 30 is joined may not necessarily be the tip 96 of the inner tube 90 but may be the inner tube shaft 95. In addition, the inner tube may be composed only of the inner tube shaft, without the tip being provided.

The balloon 30 preferably has a certain degree of flexibility and a certain degree of hardness such that the balloon 30, upon reaching a blood vessel or tissue or the like, can be inflated and can release the drug from the coating layer 32 provided on its surface. Specifically, the balloon 30 is formed from a metal or a resin, and at least the outer surface of the balloon 30 on which to provide the coating layer 32 is preferably formed of a resin. Examples of the material which can be used to constitute at least the surface of the balloon 30 include polyolefins such as polyethylene, polypropylene, polybutene, ethylene-propylene copolymer, ethylene-vinyl acetate copolymer, ionomer or mixtures of two or more of them, thermoplastic resins such as flexible polyvinyl chloride resin, polyamides, polyamide elastomers, polyesters, polyester elastomers, polyurethanes, fluororesins, etc., silicone rubbers, latex rubber, and so on. Among these, preferred are polyamides. Specifically, at least part of the surface of the inflatable portion of the medical device to be coated with the drug is formed of a polyamide. The surface of the inflatable portion formed of a polyamide provides a smooth surface. The polyamide is not particularly limited so long as it is a polymer having an amide bond. Examples of the polyamide include homopolymers such as polytetramethylene adipamide (nylon 46), polycaprolactam (nylon 6), polyhexamethylene adipamide (nylon 66), polyhexamethylene sebacamide (nylon 610), polyhexamethylene dodecamide (nylon 612), polyundecanolactam (nylon 11), polydodecanolactam (nylon 12), etc., copolymers such as caprolactam/lauryllactam copolymer (nylon 6/12), caprolactam/aminoundecanoic acid copolymer (nylon 6/11), caprolactam/ω-aminononanoic acid copolymer (nylon 6/9), caprolactam/hexamethylenediammonium adipate copolymer (nylon 6/66), etc., and aromatic polyamides such as copolymer of adipic acid and metaxylenediamine, copolymer of hexamethylene diamine and m,p-phthalic acid, etc. Further, polyamide elastomers which are block copolymers including nylon 6, nylon 66, nylon 11, nylon 12 or the like as hard segment and polyalkylene glycol, polyether, aliphatic polyester or the like as soft segment may also be used as a base material for the medical device according to the present embodiment. The above-mentioned polyamides may be used either singly or in a combination of two or more of them.

The balloon 30 is formed with the coating layer 32 either directly on the outer surface of the balloon or with a pretreatment layer such as a primer layer formed between the outer surface of the balloon and the coating layer 32, depending on a coating method which will be described later.

Next, the balloon coating apparatus 100 will be described. As illustrated in FIG. 1, the balloon coating apparatus 100 includes a rotation driving section 110 (first rotation driving section) configured to rotate the balloon 30 about the axis X of the balloon 30, a base section 120 configured to support the balloon catheter 10, and a coating section 130 provided with a dispensing tube 134 for dispensing a coating liquid and applying the coating liquid to an outer surface of the balloon 30. Further, the balloon coating apparatus 100 includes a rectilinear moving section 140 configured to move the dispensing tube 134 relative to the balloon 30, a tension section 150 (second rotation driving section) configured to apply a tensile force to the balloon 30, and a control unit 160 configured to control the balloon coating apparatus 100.

Figure 4A:
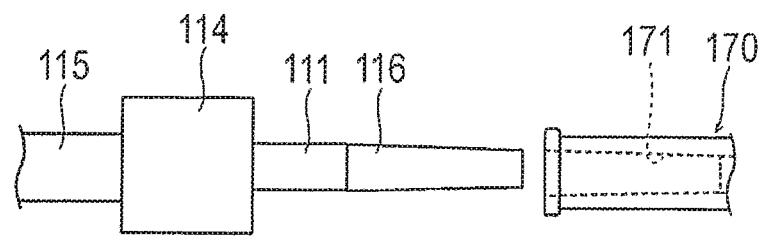
Figure 4B:
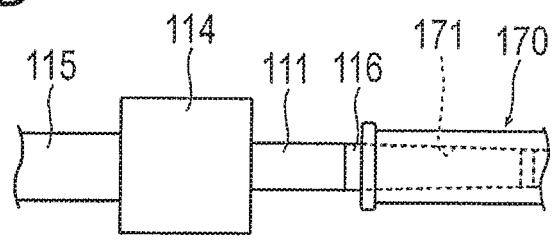

As shown in FIGS. 1, 4A and 4B, the rotation driving section 110 includes a driving shaft 111 inserted into a three-way cock 170 attached to the hub proximal opening portion 41 (see FIG. 2) of the hub 40 of the balloon catheter 10, a first motor 112 for rotating the driving shaft 111, and a first shaft joint 114 interlocking a rotary shaft 115 of the first motor 112 with the driving shaft 111. With the three-way cock 170 attached to the hub 40, it is possible to introduce the inflation fluid into the balloon 30 to inflate the balloon 30, by opening the three-way cock 170, and to maintain the inflated state of the balloon 30 by closing the three-way cock 170.

The first motor 112 is fixed to a bed 121. The driving shaft 111 is interlocked to the rotary shaft 115 of the first motor 112 by the first shaft joint 114, and is formed at a distal portion thereof with a male luer taper (projected luer taper) 116 the diameter of which decreases distally. The male luer taper 116 can be inserted into a female luer taper (recessed luer taper) 171 formed in the three-way cock 170, to be fitted to the female luer taper 171 with a frictional force. The taper ratio of the male luer taper 116 and the female luer taper 171 is prescribed in International Organization for Standardization (ISO) 594 and Japanese Industrial Standards (JIS) (commentary on standards and reference concerning medical devices), and is prescribed to be 6%. The range of insertion of the driving shaft 111 is within the range of the three-way cock 170, and the driving shaft 111 can be fitted to and detached from the three-way cock 170 easily, which is highly user friendly.

The male luer taper 116 of the driving shaft 111 may be fitted to a female luer taper which is formed not in the three-way cock 170 but at the hub proximal opening portion 41 of the hub 40. In this case, the driving shaft 111 is not inserted to the distal side beyond the hub 40. Since the driving shaft 111 is not inserted to the distal side beyond the hub 40, the catheter shaft 20 can bend flexibly, and the driving shaft 111 can be fitted to and detached from the balloon catheter 10 easily, which is highly user friendly.

The base section 120 includes the bed 121 serving as a base, and a support part 180 fixed to the bed 121 and supporting the catheter shaft 20 such that the catheter shaft 20 is rotatable. The base section 120 includes a guide groove part (guide groove) 122 holding the tension section 150 such that the tension section 150 can be moved rectilinearly, and a rack 123 having teeth aligned rectilinearly.

Figure 5:
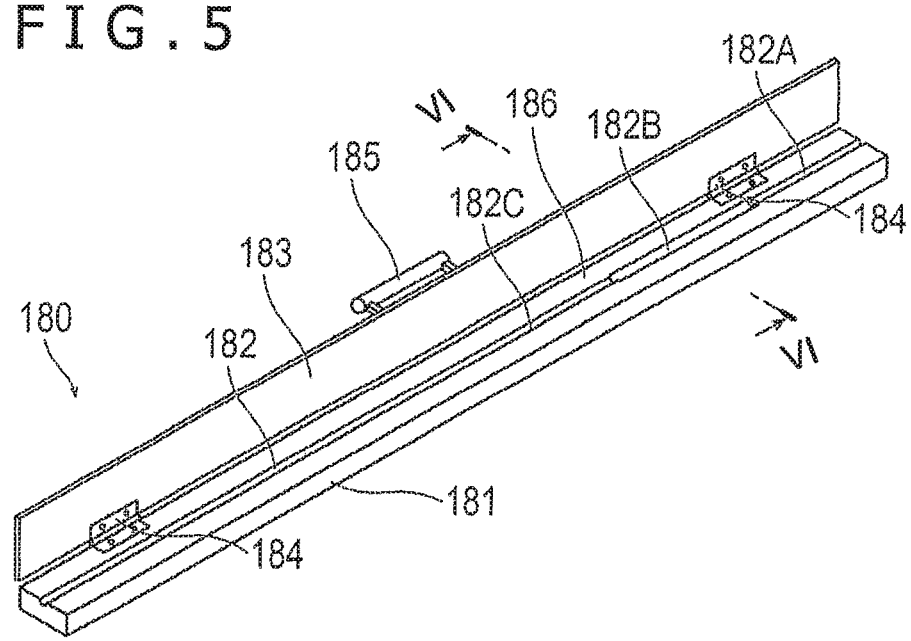
FIG. 5 is a perspective view showing a support part.
Figure 6:
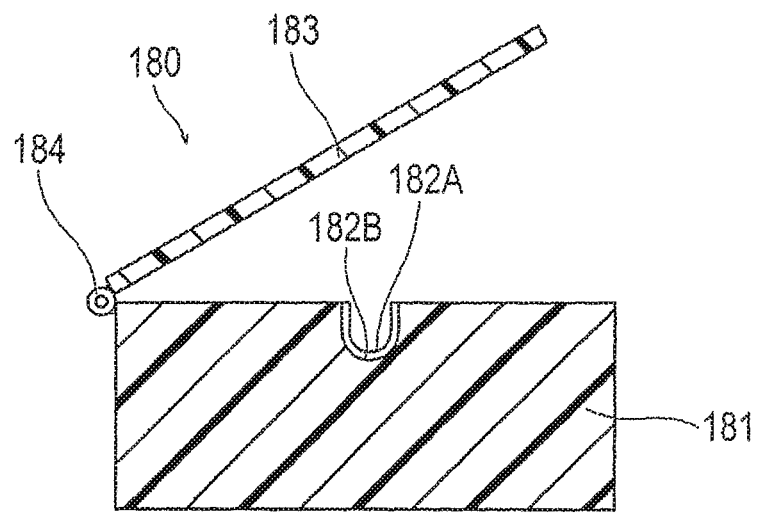
FIG. 6 is a cross-sectional view taken along the section line VI-VI of FIG. 5.

As shown in FIGS. 1, 5 and 6, the support part 180 includes a support base 181 formed with a groove portion (groove) 182 in which the catheter shaft 20 is rotatably accommodated, a lid portion (lid) 183 configured to cover a support surface 186 formed with the groove portion 182 of the support base 181, and hinge portions 184 connecting the lid portion 183 to the support base 181 such that the lid portion 183 can be opened and closed in relation to the support base 181. The lid portion 183 is provided with a handle 185 for easy grasping at the times of opening and closing the lid portion 183.

The support base 181 is formed to be elongate along the axial direction X such as to be able to support the elongate catheter shaft 20. The groove portion 182 formed in the support surface 186 includes a first groove portion 182A configured to support a part of the catheter shaft 20 that is near the balloon 30, a second groove portion 182B configured to support a range inclusive of a part of the catheter shaft 20 that is near the proximal opening portion 92, and a third groove portion 182C configured to support a portion of the catheter shaft 20 that is on the proximal side of the proximal opening portion 92. The first groove portion 182A, the second groove portion 182B and the third groove portion 182C are arranged on an extension line of the driving shaft 111, aligned in this order from the distal side. The first groove portion 182A, the second groove portion 182B and the third groove portion 182C may be located with a slight deviation to the vertically lower side from the extension line of the driving shaft 111, taking into account bending of the catheter shaft 20 due to its own weight between the driving shaft 111 and the support base 181. The second groove portion 182B is greater in width and depth than the first groove portion 181A and the third groove portion 182C, such that a part of the catheter shaft 20 near the proximal opening portion 92 that is locally projecting from the surroundings can be restrained from being damaged by friction. The groove portion formed in the support base 181 may be constant in width and depth. In addition, the groove portion formed in the support base 181 may be constant, or varies from part to part, in only one of width and depth.

The width and depth of the groove portion 182 (the first groove portion 182A, the second groove portion 182B and the third groove portion 182C) are preferably greater than the outside diameter of the catheter shaft 20 by approximately 1 mm to 5 mm. If the width and depth of the groove portion 182 are too small, the catheter shaft 20 is liable to be damaged by friction, and the load on rotation becomes large, making rotation of the balloon 30 unstable; as a result, it may be difficult to form the coating layer 32 in an appropriate amount, and it may be difficult to control, for example, the morphological form of the drug in the coating layer 32. On the other hand, if the width and depth of the groove portion 182 are too large, the catheter shaft 20 moves irregularly within the groove portion 182 upon rotation, making the rotation of the balloon 30 unstable; consequently, it may be difficult to form the coating layer 32 in an appropriate amount, and it may be difficult to control, for example, the morphological form of the drug in the coating layer 32.

The shape of the groove portion 182 has a semicircular shape at a bottom surface in cross-section orthogonal to the axial direction X in this embodiment, but this is not restrictive, and the shape may be a V shape or a tetragonal shape, for example. The shape of the groove portion 182 is preferably such as to make surface contact with the catheter shaft 20, such that the catheter shaft 20 is not liable to be damaged. Therefore, the shape of the groove portion 182 preferably does not have a projecting part, such as a W-shaped part, in cross-section orthogonal to the axial direction X.

The lid portion 183 is rotatably held on the support base 181 by the hinge portions 184, can cover the support surface 186 to close the groove portion 182, and can be separated from the support surface 186 to expose the groove portion 182. The lid portion 183 functions to maintain the catheter shaft 20, which is rotated in the groove portion 182, within the groove portion 182. The lid portion 183 preferably has a certain degree of weight such that the rotating catheter shaft 20 would not fly out of the groove portion 182, the weight being, for example, not less than 30 g. The lid portion 183 may be provided with a locking mechanism (not shown) for fixing the lid portion 183 to the support base 181. The locking mechanism may be, for example, snap fit.

The materials constituting the support base 181 and the lid portion 183 are not specifically restricted, and there can be used those materials which have a low coefficient of friction, such as PTFE (polytetrafluoroethylene) and rigid polyethylene.

As shown in FIG. 1, the tension section 150 (second rotation driving section) includes a sliding part 151 fitted to the guide groove part 122 of the base section 120, a pinion 152 meshed with the rack 123, a dial 153 for rotating the pinion 152, and a holding part 190 configured to hold the balloon catheter 10. Further, the tension section 150 includes a second motor 154 for rotating the holding part 190, and a second shaft joint 156 interlocking a rotary shaft 155 of the second motor 154 with the holding part 190.

The sliding part 151 is slidably fitted to the guide groove part 122 of the base section 120, and slides within the guide groove part 122, thereby moving the second motor 154 rectilinearly. The pinion 152 is rotated by rotational operation of the dial 153, and, by meshing with the rack 123, can move the sliding part 151 along the guide groove part 122. With the dial 153 rotated, a tensile force can be exerted on the balloon 30. The tensile force, which is not particularly limited, is preferably 5 N to 15 N, for example. If the tensile force is too small, bend of the balloon 30 cannot be straightened. If the tensile force is too large, on the other hand, the balloon 30 may be damaged by the tensile force. When the tensile force is exerted on the balloon 30, a force acts in such a direction as to disengage the male luer taper 116 of the driving shaft 111 from the female luer taper 171 of the three-way cock 170. Therefore, a fixing strength between the driving shaft 111 and the three-way cock 170 is desirably at such a level as to be able to endure the tensile force exerted, and is, for example, 10 N to 50 N. If the fixing strength between the driving shaft 111 and the three-way cock 170 is too strong, the hub 40 may be damaged when the balloon catheter 10 is detached from the apparatus. For instance, in the case of a balloon catheter 10 wherein the balloon 30 is formed of a polyamide resin, the outside diameter of the balloon 30 when inflated is 6 mm and the length of the balloon 30 is 150 mm, it has been confirmed that exertion of a force of 25 N damages the balloon 30. If the fixing strength between the driving shaft 111 and the three-way cock 170 is too weak, on the other hand, exertion of the tensile force on the balloon 30 may cause the driving shaft 111 and the three-way cock 170 to be disengaged from each other.

Instead of manual rotation of the dial 153, a motor or the like may be provided and controlled.

Figure 7:
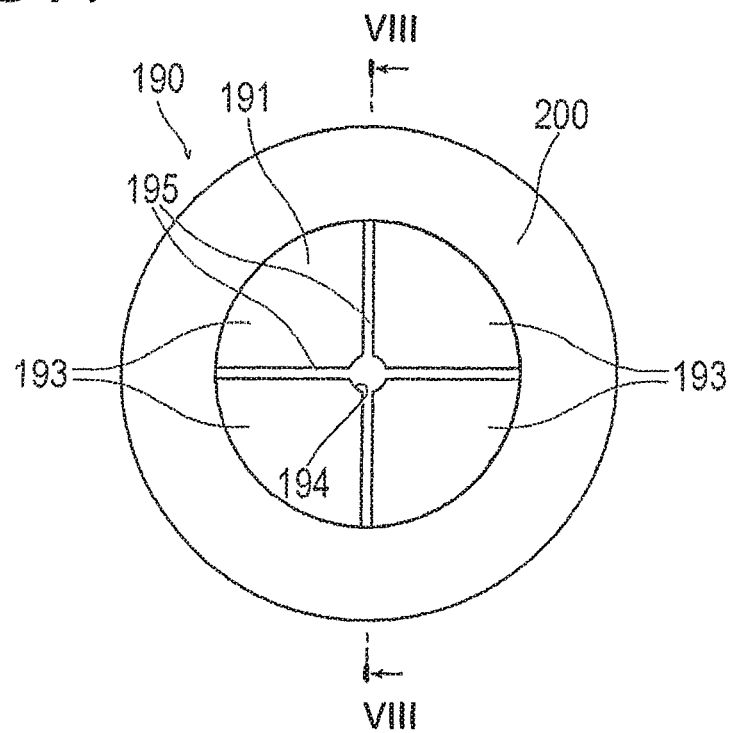
FIG. 7 is a plan view showing a holding part.
Figure 8:
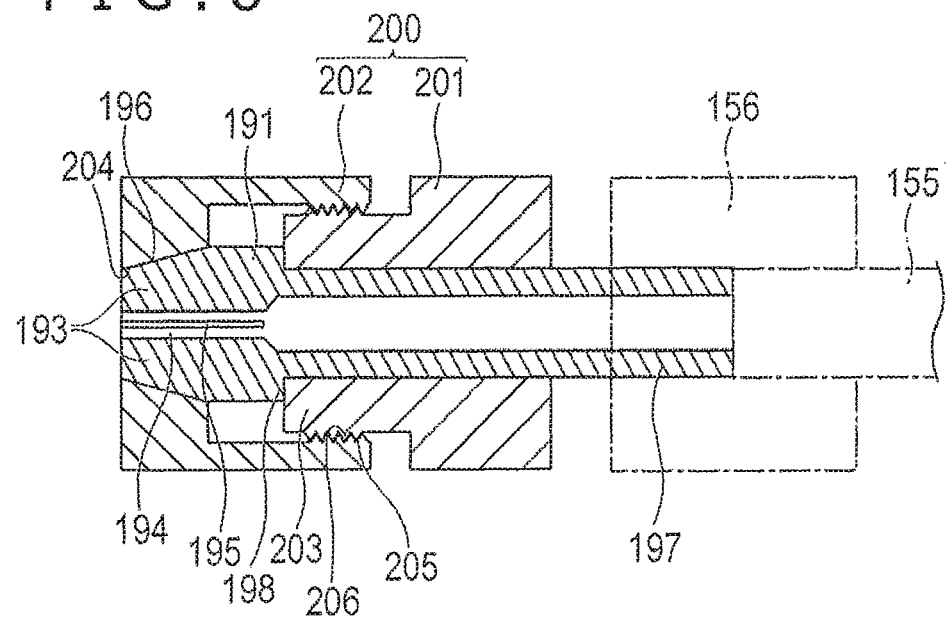
FIG. 8 is a cross-sectional view taken along the section line VIII-VIII of FIG. 7.

As shown in FIGS. 7 and 8, the holding part 190 includes a collet chuck 191, and a chuck holder 200 for holding the collet chuck 191.

The collet chuck 191 is formed therein with slits 195 such that a plurality of (in this embodiment, four) clamping portions 193 having clamping surfaces 194 shaped correspondingly to the shape of an object to be grasped are arranged in the circumferential direction of the collet chuck 191. The collet chuck 191 is formed with a tapered surface 196 at an outer circumferential surface on an end portion side where the clamping portions 193 are formed, and is formed, on the opposite side from the side where the clamping portions 193 are formed, with a interlock portion 197 configured to interlock with the second shaft joint 156. The interlock portion 197 is smaller in outside diameter than the clamping portions 193. Between the clamping portions 193 and the interlock portion 197 is formed a stepped portion 198 where outside diameter is reduced. The clamping surfaces 194 are formed of groove-shaped curved surfaces extending along the axis of the distal joint portion 34 between the balloon 30 and the inner tube 90, the joint portion 34 being grasped. The clamping surfaces 194 can clamp a portion of the side surface of the distal joint portion 34, such that deformation of the distal joint portion 34 is prevented as securely as possible. A scroll chuck, a drill chuck or an independent chuck may be used in place of the collet chuck 191, so long as the distal joint portion 34 can be clamped on a surface basis such that deformation of the distal joint portion 34 is prevented as securely as possible. In addition, the number of the clamping portions is not limited to four, so long as the number is not less than two.

The chuck holder 200 includes a first holder 201 that the interlock portion 197 of the collet chuck 191 penetrates, and a second holder 202 that the clamping portions 193 of the collet chuck 191 contact. The first holder 201 is a tube-shaped member that the interlock portion 197 of the collet chuck 191 penetrates. The first holder 201 is formed on one end side with an attachment portion 203 configured to make contact with the stepped portion 198 of the collet chuck 191 such that the stepped portion 198 is caught on the attachment portion 203, and is formed with a first screw portion 205 at an outer circumferential surface of the attachment portion 203. The second holder 202 is a tube-shaped member having a second screw portion 206 for screw engagement with the first screw portion 205, and is formed at an inner circumferential surface of the second holder 202 with a tapered push-in surface 204 for contact with the tapered surface 196 of the collet chuck 191. When the collet chuck 191 is disposed inside the first holder 201 to cause the attachment portion 203 to contact the stepped portion 198, the second screw portion 206 of the second holder 202 is put into screw engagement with the first screw portion 205 of the first holder 201 and the second holder 202 is rotated, whereby the second holder 202 is moved closer to the first holder 201. When the second holder 202 is moved closer to the first holder 201, the push-in surface 204 of the second holder 202 slides on the tapered surface 196 of the collet chuck 191, and the clamping portions 193 are deformed such that the slits 195 are narrowed, so that the clamping surfaces 194 come closer to one another. As a result, a distal portion of the balloon catheter 10 is clamped at the center of the clamping surfaces 194. The part to be clamped by the clamping portions 193 is preferably the distal joint portion 34 where the balloon 30 and the inner tube 90 of the balloon catheter 10 are joined together, but this is not restrictive, and other parts may be clamped so long as the other parts can be clamped.

Examples of materials which can be used to constitute the collet chuck 191 and the chuck holder 200 include metals such as stainless steel, aluminum, etc. and resins such as fluororesins, acrylonitrile-butadiene-styrene resin, polyethylene, etc.

Figure 9:
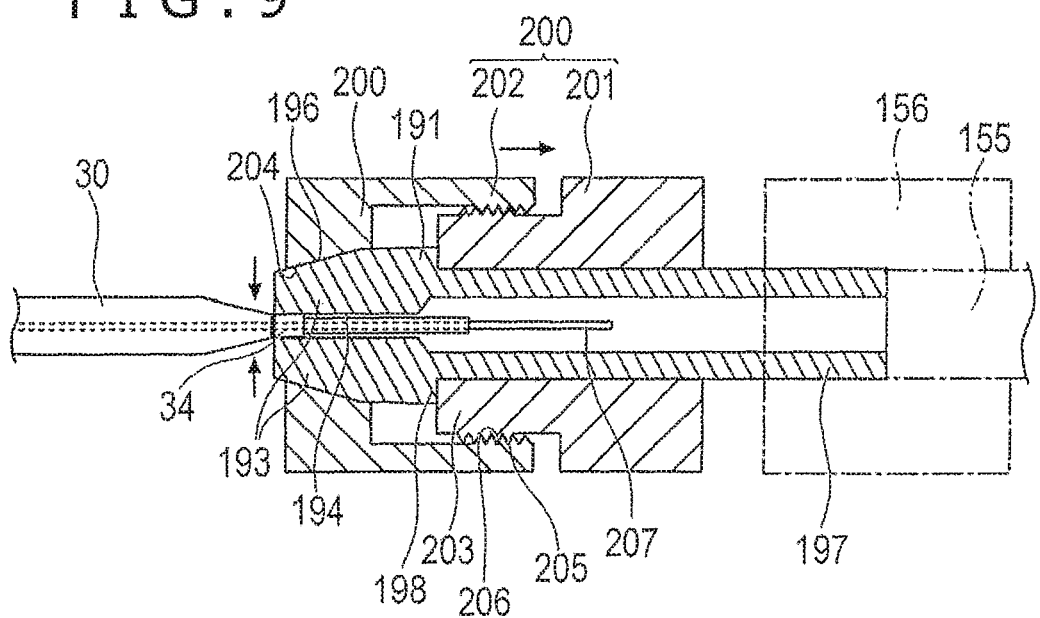
FIG. 9 is a cross-sectional view showing a state where a balloon catheter is held by the holding portion.

At the time of grasping the balloon catheter 10 by the collet chuck 191, a core member 207 is disposed in the guide wire lumen 91, as shown in FIGS. 3 and 9, in such a manner as to prevent the balloon catheter 10 from being crushed. The distal portion of the core member 207 protrudes distally beyond the distal opening portion 93 of the guide wire lumen 91, and has its proximal portion located on the proximal side of a region of inflation of the balloon 30. The protrusion length L1 of the core member 207 from the distal opening portion 93 is not particularly limited, but is preferably such a length that the core member 207 can be reliably protruded enough to restrain the balloon catheter 10 from crushing, and is, for example, 2 mm to 50 mm.

Since the distal portion of the core member 207 protrudes distally beyond the distal opening portion 93 of the guide wire lumen 91 and the proximal portion of the core member 207 is located on the proximal side of the region of inflation of the balloon 30, the core member 207 is present inside the part to be clamped by the clamping portions 193, whereby deformation of the balloon catheter 10 due to crushing is restrained.

The proximal portion of the core member 207 does not protrude proximally from the proximal opening portion 92 of the guide wire lumen 91, but is located near the proximal opening portion 92 or on the distal side of the proximal opening portion 92. The position of the proximal portion of the core member 207 is at the proximal end of the balloon inflation part (balloon fusion-bonded part 35) or on the proximal side of the proximal end of the balloon inflation part (balloon fusion-bonded part 35). The proximal portion of the core member 207 is preferably in proximity to the proximal opening portion 92. The separated distance L2 (FIG. 3) by which the proximal portion of the core member 207 is separated distally from the proximal opening portion 92 is not particularly limited, and is, for example, 0 mm to 50 mm. The proximal portion of the core member 207 may be located near the proximal opening portion 92, so long as the proximal portion of the core member 207 does not protrude proximally from the proximal opening portion 92. Since the proximal portion of the core member 207 does not protrude proximally from the proximal opening portion 92, the core member 207 can, even upon rotation of the balloon catheter 10, be restrained from interfering with external members, and, accordingly, it can be ensured that the position of the outer surface of the balloon 30 is not liable to fluctuate during rotation.

When crushing of the balloon catheter 10 is restrained and the position of the outer surface of the balloon 30 is not liable to fluctuate during rotation, it becomes possible to apply a coating liquid to the outer surface of the balloon 30 in a more appropriate quantity. Further, when the position of the outer surface of the balloon 30 is not liable to fluctuate during rotation, it becomes relatively easy to set the contact force in contact of the dispensing tube 134 with the balloon 30 to a desirable value, and it becomes possible to appropriately set, for example, the morphological form of the drug in the coating formed on the balloon 30.

A value obtained by subtracting the outside diameter of the core member 207 from the inside diameter of the guide wire lumen 91 is preferably greater than 0 and not greater than 0.5 mm. If the outside diameter of the core member 207 is too large in relation to the inside diameter of the guide wire lumen 91, the inner tube 90 in which the guide wire lumen 91 is formed is liable to be damaged by the core member 207. If the outside diameter of the core member 207 is too small in relation to the inside diameter of the guide wire lumen 91, the inner tube 90 is liable to be deformed when the inner tube 90 is clamped by the clamping portions 193.

Because the balloon catheter 10 according to this embodiment is a rapid exchange type balloon catheter, the guide wire lumen 91 does not range or extend to the hub 40, and the core member 207 is not present in the hub 40.

As shown in FIG. 1, the rectilinear moving section 140 includes a movable base 141 movable rectilinearly in a direction parallel to the axis X of the balloon 30, and a tube positioning part 142 which is disposed on the movable base 141 and is configured to move the dispensing tube 134 in a Y-axis direction and a Z-axis direction (see FIG. 10) which are orthogonal to the axis X. The movable base 141 is movable rectilinearly by a drive source, such as a motor, incorporated therein. The coating section 130 is mounted on the movable base 141, and the movable base 141 moves the coating section 130 rectilinearly in both directions along the axis X of the balloon catheter 10. The tube positioning part 142 includes a tube fixing portion 143 to which the dispensing tube 134 is fixed, and a driving portion 144 configured to move the tube fixing portion 143 in the Y-axis direction and the Z-axis direction. The driving portion 144 has a two-axis slider structure capable of movement by a drive source, such as a motor or a cylinder, incorporated therein, whereby the driving portion 144 can move the tube fixing portion 143 in both the Y-axis direction and the Z-axis direction. The Y-axis direction and the Z-axis direction in which the dispensing tube 134 is moved in a plane orthogonal to the axis X of the balloon catheter 10 may not necessarily be defined as the vertical direction and a horizontal direction.

The coating section 130 includes a vessel 131 for containing the coating liquid, a liquid feed pump 132 for feeding the coating liquid in an arbitrary feeding quantity, and the dispensing tube 134 for applying the coating liquid to the balloon 30.

The liquid feed pump 132 is, for example, a syringe pump. Under control of the control unit 160, the liquid feed pump 132 can suck the coating liquid from the vessel 131 through a suction tube 133, and can supply the coating liquid into the dispensing tube 134 through a supply tube 135 in an arbitrary feeding quantity. The liquid feed pump 132 is disposed on the movable base 141, and can be moved rectilinearly by the movement of the movable base 141. The liquid feed pump 132 is not restricted to the syringe pump so long as it can feed the coating liquid, and may be, for example, a tube pump.

Figure 10:
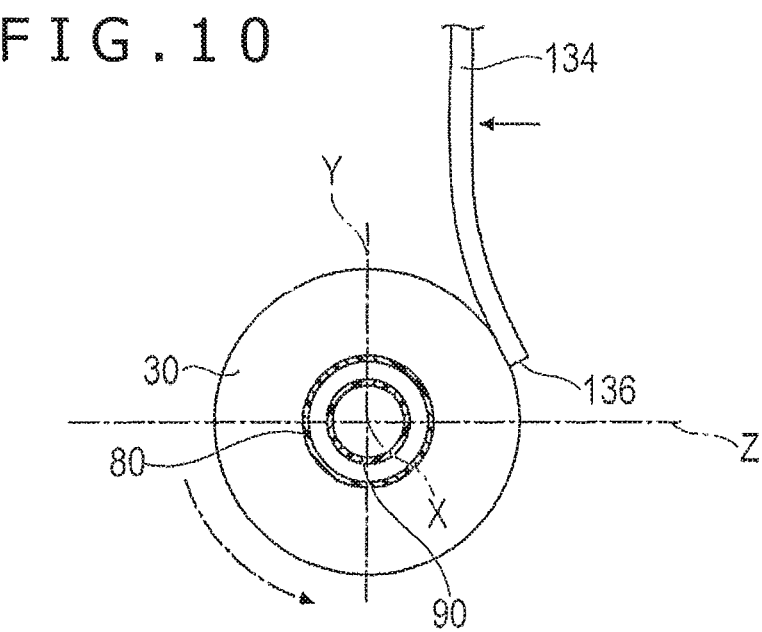
FIG. 10 is a cross-sectional view showing a balloon at the time of applying a coating liquid to an outer surface of the balloon.

The dispensing tube 134 is a member which communicates with the supply tube 135 and by which the coating liquid supplied from the liquid feed pump 132 through the supply tube 135 is ejected onto the outer surface of the balloon 30. The dispensing tube 134 is a circular tube-shaped member which is flexible. The dispensing tube 134 has its upper end fixed to the tube fixing portion 143, extends vertically downward from the tube fixing portion 143, and is formed with an opening at an ejection end 136 which is its lower end. The opening formed at the ejection end 136 is substantially perpendicularly to the axis of the dispensing tube 134. By moving the movable base 141, the dispensing tube 134 can be moved rectilinearly in both directions along the axial direction X of the balloon catheter 10, together with the liquid feed pump 132 disposed on the movable base 141. In addition, as shown in FIG. 10, the dispensing tube 134 can be moved by the driving portion 144 in two different directions (in this embodiment, the Y-axis direction which is the vertical direction and the Z-axis direction which is the horizontal direction) in a plane orthogonal to the axial direction X. A part of a side surface on an end portion side of the dispensing tube 134 (the part of a continuous length in the extending direction of the dispensing tube 134) is disposed in such a manner as to contact the outer surface of the balloon 30. The dispensing tube 134 can supply the coating liquid to the outer surface of the balloon 30, in the state of being pressed against the balloon 30 and being bent. Alternatively, a portion on the distal end portion side of the dispensing tube 134 may be preshaped to possess a bent shape (permanent bent shape) before any contact with the balloon to form a certain angle relative to the longitudinal axis of the dispensing tube 134, and a side surface of the distal end of the dispensing tube 134 thus bent or at least part of the side surface may be disposed to contact the outer surface of the balloon 30.

The dispensing tube 134 may not necessarily be circular tube-like in shape, so long as the dispensing tube 134 can supply the coating liquid. And the dispensing tube 134 may not necessarily extend in the vertical direction, so long as the dispensing tube 134 can eject the coating liquid.

The dispensing tube 134 is preferably formed of a flexible material, such that the contact load in contact with the balloon 30 can be reduced and the change of the contact position attendant on rotation of the balloon 30 can be absorbed by bending. Examples of the material which can be used to constitute the dispensing tube 134 include polyolefins such as polyethylene, polypropylene, etc., cyclic polyolefins, polyesters, polyamides, polyurethanes, and fluoroIesins such as PTFE (polytetrafluoroethylene), ETFE (tetrafluoroethylene-ethylene copolymer), PFA (tetrafluoroethylene-perfluoroalkylvinyl ether copolymer), FEP (tetrafluoroethylene-hexafluoropropylene copolymer), etc., but the material is not specifically restricted so long as the material is flexible and deformable.

The outside diameter of the dispensing tube 134 is not particularly limited, and is, for example, 0.1 mm to 5.0 mm, preferably 0.15 mm to 3.0 mm, and more preferably 0.3 mm to 2.5 mm. The inside diameter of the dispensing tube 134 is not specifically restricted, and is, for example, 0.05 mm to 3.0 mm, preferably 0.1 mm to 2.0 mm, and more preferably 0.15 mm to 1.5 mm. The length of the dispensing tube 134 is not particularly limited, and is preferably a length of up to 5 times the diameter of the balloon; specifically, the length is, for example, 1.0 mm to 50 mm, preferably 3 mm to 40 mm, and more preferably 5 mm to 35 mm.

The control unit 160 is composed, for example, of a computer, and generally controls the rotation driving section 110, the rectilinear moving section 140, the tension section 150 and the coating section 130. The control unit 160 can cause the first motor 112 of the rotation driving section 110 and the second motor 154 of the tension section 150 to rotate synchronously at the same rotational speed. In addition, the control unit 160 can generally control the rotational speed of the balloon 30, initial positioning of the dispensing tube 134 relative to the balloon 30, the moving speed of the dispensing tube 134 in the axial direction X relative to the balloon 30, the ejection rate of the drug from the dispensing tube 134, and the like.

The coating liquid contains a water-insoluble drug and a solvent. After the coating liquid is supplied to the outer surface of the balloon 30, the solvent is volatilized, whereby a coating layer 32 having a crystalline layer or an amorphous layer is formed on the outer surface of the balloon 30. The balloon 30 and the coating layer 32 can be used as a drug eluting balloon for gradually eluting the drug in a living body.

The water-insoluble drug herein means a drug which is insoluble or difficultly soluble in water; specifically, the solubility of the water-insoluble drug in water is less than 5 mg/mL at pH 5 to 8. The solubility may be less than 1 mg/mL, or, further, less than 0.1 mg/mL. The water-insoluble drug includes fat-soluble drug.

Some examples of the preferred water-insoluble drug include immunosuppressant, for example, cyclosporines inclusive of cyclosporine, immunoadjuvant such as rapamycin, etc., carcinostatic agent such as paclitaxel, etc., antiviral or antibacterial agent, antineoplastic agent, analgesic agent, anti-inflammatory agent, antibiotic, antiepileptic, anxiolytic agent, antiparalytic agent, antagonist, neuron blocking agent, anticholinergic agent, cholinergic agent, muscarine antagonist, muscarinic agent, antiadrenergic agent, antiarrhythmic agent, antihypertensive agent, hormone preparation, and nutritional supplement.

The water-insoluble drug is preferably at least one selected from rapamycin, paclitaxel, docetaxel, and everolimus. The rapamycin, paclitaxel, docetaxel and everolimus herein include their analogs and/or derivatives so long as the analogs and/or derivatives have equivalent drug activity to the original. For example, paclitaxel and docetaxel are in an analog relation. Rapamycin and everolimus are in a derivative relation. Among these, more preferable is paclitaxel.

The water-insoluble drug may further contain an excipient. The excipient is not particularly restricted so long as it is pharmaceutically acceptable. Examples of the excipient include water-soluble polymer, sugar, contrast agent, citric acid ester, amino acid ester, glycerol ester of short-chain monocarboxylic acid, and salts and surfactants that are pharmaceutically acceptable.

The excipient is preferably small in amount based on the water-insoluble drug, and preferably does not form a matrix. The excipient preferably does not contain, but may contain, micelle, liposome, contrast agent, emulsifier or surfactant. Further, the excipient preferably does not contain polymer but contains only low molecular compounds.

The solvent is not particularly limited. Examples of the solvent include tetrahydrofuran, ethanol, glycerin (also called glycerol or propane-1,2,3-triol), acetone, methanol, dichloromethane, hexane, ethyl acetate and water. Among these, preferred are mixed solvents of some of tetrahydrofuran, ethanol, acetone and water.

Now, a balloon coating method for forming a coating layer 32 containing the water-insoluble drug on a surface of the balloon 30 by use of the aforementioned balloon coating apparatus 100 will be described below.

First, the three-way cock 170 is interlocked to the hub proximal opening portion 41 of the hub 40 of the balloon catheter 10, an inflation fluid is caused to flow into the balloon 30 by opening the three-way cock 170 and using a syringe or the like, to thereby inflate the balloon 30, and after the balloon is inflated, the three-way cock 170 is closed to maintain the inflated state of the balloon 30. A coating layer 32 can also be formed on the surface of the balloon 30 without inflating the balloon 30, and, in that case, it is unnecessary to supply the inflation fluid into the balloon 30.

Next, the lid portion 183 of the support base 181 is opened, the catheter shaft 20 is accommodated in the groove portion 182, and the lid portion 183 is closed. The shaft 20 is accommodated in the groove portion 182 while the core member 207 is positioned in the guide wire lumen 91. The proximal opening portion 92 of the catheter shaft 20 is accommodated in the second groove portion 182B, which is greater than the first groove portion 182A and the third groove portion 182C in width and depth.

Subsequently, the male luer taper 116 of the driving shaft 111 is inserted into and interlocked to the female luer taper 171 of the three-way cock 170. This results in that a rotating force can be applied to the proximal portion of the balloon catheter 10 from the first motor 112.

Next, in the condition where the clamping portions 193 of the collet chuck 191 are opened wider than the distal joint portion 34 of the balloon catheter 10, the distal joint portion 34 of the balloon catheter 10 is inserted into the inside of the clamping portions 193. Thereafter, the second holder 202 is rotated relative to the first holder 201, whereon the second holder 202 is moved closer to the first holder 201, the push-in surface 204 of the second holder 202 slides on the tapered surface 196 of the collet chuck 191, and the clamping portions 193 are deformed in such a manner as to move toward the center. This results in that the clamping surfaces 194 come closer to one another, and the distal joint portion 34 of the balloon catheter 10 is clamped by the clamping surfaces 194. Consequently, it becomes possible to apply a rotating force to the distal portion of the balloon catheter 10 from the second motor 154.

The order in which the balloon catheter 10 is disposed on the driving shaft 111, the collet chuck 191 and the support base 181 is not particularly limited.

Subsequently, the dial 153 is rotated to move the second motor 154 and the collet chuck 191 distally, whereon a tensile force acts on the balloon 30, whereby bend of the balloon 30 is straightened.

Next, the dispensing tube 134 is positioned relative to the balloon 30. First, the position of the movable base 141 is adjusted, to perform positioning of the dispensing tube 134 with respect to the X-axis direction. In this instance, the dispensing tube 134 is positioned so that the dispensing tube 134 is located on the distalmost side of a region where the coating layer 32 is formed on the balloon 30.

Subsequently, the driving portion 144 is operated to move the dispensing tube 134, such that the dispensing tube 134 contacts the balloon 30, as shown in FIG. 10. At the position where the dispensing tube 134 contacts the balloon 30, the balloon 30 is rotated in a direction reverse to the ejection direction in which the coating liquid is ejected from the dispensing tube 134. Thus, in FIG. 10, the ejection direction in which the coating liquid is ejected from the dispensing tube 134 is downward/clockwise, while the balloon 30 is rotated in the counter-clockwise direction.

The dispensing tube 134 approaches the outer surface of the balloon 30, and contacts the balloon 30 while bending by being pressed against the balloon 30 or without bending due to such pressing. In this instance, a side surface on the end portion side of the dispensing tube 134 is configured to contact the surface of the balloon 30, by so arranging the components.

Next, the coating liquid is supplied to the dispensing tube 134 while controlling the liquid feed amount by the liquid feed pump 132, and the balloon catheter 10 is rotated by exerting driving forces on both a distal portion and a proximal portion of the balloon catheter 10 by the first motor 112 and the second motor 154. That is, the one motor 112 exerts a driving force on the proximal portion of the balloon catheter 10 to rotate the balloon catheter 10 in one direction and the other motor 154 exerts a driving force on the distal portion of the balloon catheter 10 to rotate the balloon catheter 10 in the same direction, thus rotating the balloon catheter 10 in the one direction. Then, the movable base 141 is moved to gradually move the dispensing tube 134 proximally along the X-direction. Since the dispensing tube 134 is moved relative to the balloon 30, the coating liquid ejected from the opening portion of the dispensing tube 134 is applied to the outer circumferential surface of the balloon 30 while drawing a spiral. That is, the coating liquid is applied to the outer peripheral surface of the balloon 30 in a spiral fashion. In this case, after the outer surface of the balloon 30 is coated with the coating liquid at a position rotated in the direction (in this embodiment, upward direction in FIG. 10) reverse to the ejection direction of the coating liquid of the dispensing tube 134 (reverse to the extending direction of the dispensing tube 134) so as to complete forming a morphological form of crystals of the water-insoluble drug, the part coated with the coating liquid does not contact other member (for example, a dispensing tube 134 whose extending direction coincides with or is reverse to the rotating direction). In this coating method in which the direction of ejection/coating is reverse to the direction of rotation, the dispensing tube contacts and traces the part coated with the coating solution around a position on a circumference of a balloon during coating. Tracing the wet part with a dispending tube helps generate crystal cores. Since the part coated with the coating liquid does not contact, for example, a dispensing tube 134 whose extending direction (direction of ejection of the coating liquid) coincides with the rotating direction, it is possible to eliminate the possibility of hampering the formation of "a morphological form wherein crystals of the water-insoluble drug include a plurality of elongate bodies having independent long axes," and it is possible to preclude the possibility of breakage of the morphological form after the formation.

The moving speed of the dispensing tube 134 is not particularly limited, and is, for example, 0.01 mm/second to 2 mm/second, preferably 0.03 mm/second to 1.5 mm/second, and more preferably 0.05 mm/second to 1.0 mm/second. The ejection rate of the coating liquid from the dispensing tube 134 is not specifically restricted, and is, for example, 0.01 µL/second to 1.5 µL/second, preferably 0.01 µL/second to 1.0 µL/second, and more preferably 0.03 µL/second to 0.8 µL/second. The rotational speed of the balloon 30 is not particularly limited, and is, for example, 10 rpm to 300 rpm, preferably 30 rpm to 250 rpm, and more preferably 50 rpm to 200 rpm. The first motor 112 and the second motor 154 can be synchronously rotated within these ranges of rotational speed. The diameter of the balloon 30 at the time of coating the balloon 30 with the coating liquid is not specifically restricted, and is, for example, 1 mm to 10 mm, preferably 2 mm to 7 mm.

When the balloon catheter 10 is rotated, a balloon main body portion is rotated within the groove portion 182 of the support base 181. In this case, since the proximal opening portion 92 partially projecting from the surroundings, of the catheter shaft 20, is accommodated in the second groove portion 182B formed to be larger than the first groove portion 182A and the third groove portion 182C in width and depth, damage to the proximal opening portion 92 due to friction can be restrained. In addition, since the groove portion 182 is covered with the lid portion 183, the catheter shaft 20 can be restrained from flying out of the groove portion 182, and the balloon 30 can be rotated in a stable manner.

When the balloon catheter 10 is rotated, the balloon 30 may, in some cases, become eccentric due to bending along the axial direction X of the balloon 30. Since the dispensing tube 134 is flexible, however, even if the balloon 30 becomes eccentric, the dispensing tube 134 moves as well and follows the balloon 30, whereby good contact of these members is maintained. Consequently, variations in the thickness of the coating liquid applied can be restrained, and it becomes relatively easy to control the thickness and the morphological form of the coating layer 32.

Thereafter, the solvent contained in the coating liquid applied to the surface of the balloon 30 is volatilized, and the coating layer 32 containing the water-insoluble drug is formed on the surface of the balloon 30. The volatilization time is appropriately set according to the solvent, and is, for example, approximately several seconds to several hundreds of seconds.

The amount of the drug contained in the coating layer 32 is not particularly limited. The amount, in density, is 0.1 µg/mm$^2$ to 10 µg/mm$^2$, preferably 0.5 µg/mm$^2$ to 5 µg/mm$^2$, more preferably 0.5 µg/mm$^2$ to 4 µg/mm$^2$, and further preferably 1.0 µg/mm$^2$ to 3.5 µg/mm$^2$.

In addition, since the extending direction toward the ejection end 136 of the dispensing tube 134 (ejection direction) is reverse to the rotating direction of the balloon 30, the water-insoluble drug in the coating layer 32 formed on the outer surface of the balloon 30 includes a morphological form wherein the crystals include a plurality of elongate bodies having independent long axes.

The coating layer 32 having the morphological form wherein the crystals include a plurality of elongate bodies having independent long axes contains the plurality of elongate bodies in the state of forming mutually independent elongate body shapes on the substrate (the outer surface of the balloon 30). The plurality of elongate bodies may extend substantially outward in the circumferential direction with respect to the balloon surface, or may be arranged in directions substantially parallel to the circumferential direction. The plurality of elongate bodies may be present in the state of combination of these arrangements, or may be present in contact with each other such that the adjacent elongate bodies form different angles. The plurality of elongate bodies may be located with spaces (spaces not containing the crystal) therebetween on the balloon surface. Specifically, a preferable coating layer is a layer wherein a plurality of elongate bodies each composed of the crystal of the water-insoluble drug and having a long axis are present in a brush-like pattern. The plurality of elongate bodies are arranged in a circumferential and brush-like pattern on the surface of the substrate. Each of the elongate bodies is present independently, and has a certain length, with one end (proximal end) of the length part being fixed to the substrate surface. The elongate body does not form a composite structure, and is not interlocked, with the adjacent elongate bodies. The long axis of the crystal is substantially rectilinear. The elongate body forms a predetermined angle with the substrate surface intersecting with the long axis thereof. The predetermined angle here is in the range of from 45 degrees to 135 degrees, preferably 70 degrees to 110 degrees, and more preferably 80 degrees to 100 degrees. Further preferably, the long axis of the elongate body forms an angle of substantially 90 degrees with the substrate surface. The elongate body, at least its portion near the distal end thereof, is hollow. A section of the elongate body in a plane orthogonal to the long axis of the elongate body has a void (hollow portion). In the elongate body thus having a void, the section of the elongate body in a plane orthogonal to the long axis is polygonal in shape. The polygon here is, for example, a tetragon, a pentagon, a hexagon or the like. Therefore, the elongate body is formed as an elongate polyhedron that has a distal end (or distal end surface) and a proximal end (or proximal end surface), wherein a side surface portion between the distal end (or distal end surface) and the proximal end (or proximal end surface) is composed of a plurality of substantially plane surfaces. This crystalline morphological form (hollow, elongate crystalline morphological form) constitutes the whole body or at least part of a plane surface on the substrate surface.

The layer having the morphological form including the hollow elongate crystals is characterized as follows.

(1) A plurality of elongate bodies (rod-shaped bodies) having independent long axes, wherein the elongate bodies are hollow. The elongate bodies are rod-like in shape (rod-shaped).

(2) The elongate bodies having long axes, wherein many of the elongate bodies are polyhedrons of which the section in a plane orthogonal to the long axis is a polygon. Of the elongate crystals, not less than 50% by volume are elongate polyhedrons. Side surfaces of the polyhedrons are mainly tetrahedron. In some cases, the elongate polyhedron has a plurality of surfaces (grooves) formed at a reentrant angle with a vertex extending in the long axis direction. The reentrant angle here means that at least one of the internal angles of the polygon of the section of the elongate body in a plane orthogonal to the long axis is an angle greater than 180 degrees.

(3) The elongate bodies having the long axes are elongate polyhedrons in many cases. When viewed in a plane orthogonal to the long axis of the elongate body, the section of the elongate body is a polygon, which is observed as a tetragon, a pentagon or a hexagon.

(4) The plurality of elongate bodies having independent long axes are aligned with the long axes at angles in a predetermined range, preferably in the range of from 45 degrees to 135 degrees, against the substrate surface. In other words, the plurality of elongate bodies having independent long axes stand together substantially uniformly on the substrate surface. The region in which the elongate bodies stand together extend in the circumferential direction and the axial direction of the substrate surface and is formed substantially uniformly. The angles of the independent elongate bodies against the substrate surface may be different or the same within the predetermined range.

(5) Each of the elongate bodies having the independent long axes has its one end (proximal end) of the length part thereof fixed to the substrate surface.

(6) The morphology of a part near the substrate surface, of the elongate body, may in some cases be a stack of granular, short rod-shaped or short curved line-shaped crystals. Some of the elongate bodies having the long axes have their long axes directly or indirectly on the substrate surface. Therefore, in some cases, the elongate bodies having the long axes stand together on the above-mentioned stack.

(7) The length of the elongate bodies having the long axes in the axial direction is preferably 5 µm to 20 µm, more preferably 9 µm to 11 µm, and further preferably around 10 µm. The diameter of the elongate bodies having the long axes is preferably 0.01 µm to 5 µm, more preferably 0.05 µm to 4 µm, and further preferably 0.1 µm to 3 µm.

(8) On the surface of the layer containing the hollow elongate body crystalline morphological form, there is no other morphological form (for example, an amorphous plate-shaped morphological form) mixed in therewith. Not less than 50% by volume, more preferably not less than 70% by volume, of the crystals have the crystalline morphological forms of the above (1) to (7). Further preferably, substantially all the crystals have the crystalline morphological form of the above (7).

(9) In the hollow elongate body crystalline morphological form, other compound or compounds can be present in the coating layer containing the water-insoluble drug constituting the crystals. In that case, the other compound or compounds are present in the state of being distributed into spaces between the plurality of crystals (elongate bodies) of the water-insoluble drug that stand together on the substrate surface of the balloon. As for the proportions of the substances constituting the coating layer, in this case, the proportion (in percent by volume) of the crystals of the water-insoluble drug is by far greater than the proportion of the other compound or compounds.

(10) In the hollow elongate body crystalline morphological form, the water-insoluble drug constituting the crystals exists on the substrate surface of the balloon. In the coating layer on the balloon substrate surface that has the water-insoluble drug constituting the crystals, no matrix including the excipient is formed. Therefore, the water-insoluble drug constituting the crystals is not adhered in the matrix material. The water-insoluble drug constituting the crystals is even not embedded in a matrix material.

(11) In the hollow elongate body crystalline morphological form, the coating layer may contain crystal particles of the water-insoluble drug that are regularly disposed on the substrate surface and excipient particles of an excipient that are irregularly disposed between the crystal particles. In this case, the molecular weight of the excipient is smaller than the molecular weight of the water-insoluble drug. Therefore, the proportion of the excipient particles per a predetermined area of the substrate is smaller than the proportion of the crystal particles, and, accordingly, the excipient particles do not form a matrix. Here, the crystal particles of the water-insoluble drug may be one of the above-mentioned elongate bodies, the excipient particles are present in the state of being by far smaller than the crystal particles of the water-insoluble drug and dispersed between the crystal particles of the water-insoluble drug; accordingly, in some cases, the excipient particles may not be observed in a scanning electron microscope (SEM) image or a laser microphotograph.

The crystal layer of the hollow elongate body morphological form, when delivered into a living body as a coating layer formed by coating a substrate surface of a medical device with the drug, is low in toxicity and high in stenosis inhibitory effect. The present inventors consider that the reason for this lies in that the solubility of the drug having a certain crystal morphology after transfer to tissue and the property for being retained in the tissue have influences on these characteristic properties. The water-insoluble drug including the hollow elongate body crystal morphology, upon transfer to the tissue, is reduced in the size of one unit of crystal; therefore, the drug is high in the property for permeation into the tissue. In addition, the water-insoluble drug is high in solubility in the tissue. The high permeation property and high solubility permit the drug to act effectively, whereby stenosis can be inhibited. The drug is considered to be low in toxicity because the drug is less liable to remain as large lumps in the tissue.

In addition, the layer including the hollow elongate body crystalline morphological form is a morphological form wherein substantially uniform elongate bodies having long axes stand together substantially uniformly and regularly on the substrate surface. Therefore, the size (the length in the long axis direction) of the crystals transferred to the tissue is as small as approximately 10 µm. For this reason, the drug acts uniformly on the lesion affected area, and its property for permeation into the tissue is enhanced. Further, since the crystals transferred to the tissue are small in size, a situation in which an excess amount of the drug would be retained in the lesion affected area for an excess time is obviated. For this reason, the drug is considered to be able to show a high stenosis inhibitory effect, without exhibiting toxicity.

Where the extending direction of the dispensing tube 134 or the ejection direction of the coating liquid is reverse to the rotating direction of the balloon 30, the water-insoluble drug in the coating layer 32 acquires a morphological form including the hollow elongate body crystalline morphological form. The principle of this phenomenon may be considered to lie, for example, in that the coating liquid ejected from the ejection end 136 onto the balloon 30 is stimulated by the dispensing tube 134 due to the rotation. In addition, in the condition where a part of a side surface on the end portion side of the dispensing tube 134 (a part of the continuous length in the extending direction of the dispensing tube 134) is in contact with the outer surface of the balloon 30, the coating liquid is ejected from the ejection end 136 onto the balloon 30. Consequently, appropriate contact can be realized between the dispensing tube 134 and the balloon 30, such as to give the morphological form wherein the crystals of the water-insoluble drug include a plurality of elongate bodies having independent long axes.

The coating liquid is ejected from the ejection end 136 onto the balloon 30, in a region in which the balloon 30 is rotated toward the upper side in the vertical direction. For this reason, the extending direction of the dispensing tube 134, which extends downward such as to ensure easy ejection of the coating liquid, can be easily set to be reverse to the rotating direction of the balloon 30.

If the material constituting the dispensing tube 134 coming into contact with the balloon 30 is polyolefin (fluorine-free polyolefin) such as polyethylene, polypropylene, etc., the dispensing tube 134 is lower in organic solvent resistance but is higher in affinity for organic solvents and smaller in contact angle with organic solvent, as compared to a tube made of fluororesin such as PTFE. Accordingly, the coating liquid is less liable to be repelled due to the characteristic properties of the material of the dispensing tube 134 at the ejection end 136 and at the part of contact with the balloon 30. Therefore, coating unevenness is less liable to occur in coating the outer surface of the balloon 30 with the coating liquid, and the uniformity of the coating layer 32 can be controlled with high accuracy. Specifically, using a material not so high as fluororesin in organic solvent resistance for the dispensing tube 134, it is possible to lower the possibility of unevenness in coating the outer surface of the balloon 30 with the coating liquid. In addition, where the material constituting the dispensing tube 134 is polyolefin such as polyethylene, polypropylene, etc., it is also possible to cause unevenness in coating the outer surface of the balloon 30 with the coating liquid, by controlling at least one of the moving speed of the dispensing tube 134, the ejection rate of the coating liquid, and the rotational speed of the balloon 30. For this reason, by forming the dispensing tube 134 from polyolefin such as polyethylene or polypropylene, it is possible to freely control the level of uniformity of the coating layer 32.

If the material constituting the dispensing tube 134 is fluororesin such as PTFE, ETFE, PFA, FEP, etc., affinity for organic solvents is low and contact angle with organic solvent is large. Accordingly, the coating liquid is strongly repelled due to the characteristic properties of the material of the dispensing tube 134 at the ejection end 136 and at the contact part with the balloon 30. Therefore, it is possible to easily cause unevenness (nonuniformity) in coating the outer surface of the balloon 30 with the coating liquid. Where the unevenness in coating with the coating liquid is heavy, it is possible to increase the amount of the drug actually applied to some parts, while keeping constant the total amount of the drug contained in the coating layer 32 formed on the balloon 30. By this, it is possible to cause the drug to act effectively, without increasing the burden on the living body. The unevenness in coating is preferably a regular nonuniformity and is preferably a stripe pattern (spiral linear body) in which linearly coated parts are aligned in the axial direction X of the balloon 30. By applying the coating liquid while rotating the balloon 30 relative to the dispensing tube 134, the coating layer 32 can be easily formed while producing unevenness of coating in a stripe pattern. Unevenness of coating is not restricted to the form of a stripe pattern; for example, a state where extremely shaded phases are formed may be adopted.

In the coating step, it is also possible to control the uniformity of the coating layer 32, by using both a dispensing tube 134 formed of polyolefin and another dispensing tube 134 formed of fluororesin and utilizing the aforementioned different characteristic properties of the resin materials. In the case of using both the dispensing tubes 134 having the different characteristic properties, for example, at the time of sequentially coating balloons 30 of a plurality of balloon catheters 10, a control of changing the dispensing tube 134 according to the balloon 30 can be carried out. In addition, a control of changing the dispensing tube 134 depending on the part being coated of one balloon 30 can also be performed.

The drug in the coating on the outer surface of the balloon 30 can assume different morphological forms such as crystalline form, amorphous form, and mixed forms thereof. In the case where the drug is of the crystalline form, there exist various morphological forms which differ in crystal structure. Further, crystals and amorphous phases may be disposed regularly in the coating layer 32, or may be disposed irregularly in the coating layer 32.

With the dispensing tube 134 gradually moved in the axial direction X of the balloon 30 while rotating the balloon 30, the coating layer 32 is formed on the outer surface of the balloon 30 gradually along the axial direction X. After the range of the part to be coated of the balloon 30 is entirely formed thereon with the coating layer 32, the rotation driving section 110, the tension section 150, the rectilinear moving section 140 and the coating section 130 are stopped.

Thereafter, the balloon catheter 10 is dismounted from the balloon coating apparatus 100, and the coating of the balloon 30 is completed.

As described above, the balloon coating method according to the first embodiment is a balloon coating method for forming a coating layer 32 containing a water-insoluble drug on an outer surface of a balloon 30 of a balloon catheter 10, wherein the method includes: fitting a driving shaft 111 for rotating the balloon catheter 10 to an opening portion of a three-way cock 170 (interlock member) attached to a proximal portion of a hub 40 of the balloon catheter 10 and fixing the driving shaft 111 in situ by a frictional force; and rotating the balloon 30 about the axis X of the balloon 30 by the driving shaft 111 and applying a coating liquid containing the drug to the outer surface of the balloon 30. In the balloon coating method configured as above, since the driving shaft 111 is fitted and fixed to the opening portion formed in the three-way cock 170, the hub 40 is rotated about the center axis of the driving shaft 111, and, therefore, the balloon 30 can be rotated while being prevented as securely as possible from whirling. For this reason, the position of the outer surface of the balloon 30 is not liable to fluctuate during rotation, and the coating liquid can be applied to the outer surface of the balloon 30 in an appropriate quantity. In addition, since the position of the outer surface of the balloon 30 is not liable to fluctuate during rotation, the contact force in contact of the dispensing tube 134 with the balloon 30 can be easily set to a desirable value, so that, for example, the morphological form of the drug in the coating formed on the balloon 30 can be set appropriately. Note that the interlock member is not limited to the three-way cock 170, and may, for example, be a member produced for exclusive use.

In addition, since the driving shaft 111 is interlocked to the three-way cock 170 (interlock member) by a frictional force, the three-way cock 170 is disengaged from the driving shaft 111 when a predetermined tensile force is exerted thereon. Therefore, the three-way cock 170 is disengaged from the driving shaft 111 before an excessive force acts on the balloon 30 to damage the balloon 30; thus, damaging of the balloon 30 can be inhibited.

According to the balloon coating method described above, in the application of the coating liquid, the coating liquid containing the drug is applied to the outer surface of the balloon 30 while exerting on the balloon 30 a tensile force pulling the balloon 30 in the axial direction X of the balloon 30. As a result, any bend of the balloon 30 is straightened by the tensile force, a rotating force transmitted from the hub 40 capable of stable rotation is stably transmitted to the balloon 30, whereby it can be ensured that the position of the outer surface of the balloon 30 is further less liable to fluctuate during rotation. Therefore, the coating liquid can be applied to the outer surface of the balloon 30 in a more appropriate quantity. In addition, the contact force in contact of the dispensing tube 134 with the balloon 30 can be easily set to a desirable value. Accordingly, for example, the morphological form of the drug in the coating formed on the balloon 30 can be set more appropriately.

According to the balloon coating method described above, in the fixing of the proximal portion of the hub 40, the driving shaft 111 formed with the male luer taper 116 having a shape according to the female luer taper 171 formed at the opening portion of the three-way cock 170 (interlock member) is fitted and fixed to the female luer taper 171. As a result, it is possible to position the three-way cock 170 relative to the driving shaft 111 accurately and easily, to stabilize the rotation, and to ensure that the position of the outer surface of the balloon 30 is not liable to fluctuate during rotation. In addition, by applying male luer tapers 116 prescribed by the standards to the driving shaft 111, a variety of balloon catheters 10 produced adopting female luer tapers 171 prescribed by the standards can be rotated by the driving shaft 111.

Because the interlock member is a three-way cock 170, it is possible to interlock the driving shaft 111 to the hub 40 through the three-way cock 170, while ensuring that fluid can be caused to flow into and out of the balloon 30 through the three-way cock 170 by changing over a cock element of the three-way cock 170.

Further, the balloon coating method according to the first embodiment is a balloon coating method for forming a coating layer 32 containing a water-insoluble drug on an outer surface of a balloon 30 of a balloon catheter 10, wherein the method includes: inserting a core member 207 into a guide wire lumen 91 penetrating the balloon 30, disposing a proximal portion of the core member 207 on the proximal side of an inflation region of the balloon 30 (a cylindrical portion 31 and tapered portions 33 on both sides thereof), with a distal portion of the core member 207 protruding distally beyond a distal opening portion 93 of the guide wire lumen 91, and fixing by clamping together with the core member 207 a part of the balloon catheter 10 that is on a distal side of the region of inflation of the balloon 30; and moving a dispensing tube 134 for supplying a coating liquid containing the drug relative to the balloon 30 in an axial direction X of the balloon 30, while rotating the balloon 30 about the axis X of the balloon 30, to thereby apply the coating liquid to the outer surface of the balloon 30. According to the balloon coating method configured as above, the distal portion of the core member 207 protrudes distally beyond the distal opening portion 93 of the guide wire lumen 91 and the part of the balloon catheter 10 that is on the distal side of the region of inflation of the balloon 30 is fixed by clamping it together with the core member 207, and, therefore, deformation due to crushing of the balloon catheter 10 is inhibited from occurring at the time of the clamping. Further, since the proximal portion of the core member 207 is located on the proximal side of the inflation region of the balloon 30, the shape of the balloon 30 is effectively straightened by the core member 207. Therefore, deformation and damaging of the balloon catheter 10 can be restrained. In addition, the position of the outer surface of the balloon 30 is not liable to fluctuate during rotation, and, accordingly, the coating liquid can be applied to the outer surface of the balloon 30 in an appropriate quantity. In addition, since the position of the outer surface of the balloon 30 is not liable to fluctuate during rotation, the contact force in contact of the dispensing tube 134 with the balloon 30 can be easily set to a desirable value. Consequently, for example, the morphological form of the drug in the coating formed on the balloon 30 can be set appropriately.

In the balloon coating method as above, the balloon catheter 10 is of a rapid exchange type. During the fixing of the balloon catheter 10, the balloon catheter 10 is fixed, with the proximal portion of the core member 207 disposed on the distal side of the proximal opening portion 92 of the guide wire lumen 91 without protruding from the proximal opening portion 92. This helps ensure that the core member 207 does not interfere with surrounding members or the like when the balloon catheter 10 is rotated, and that the position of the outer surface of the balloon 30 is not liable to fluctuate during rotation. Therefore, the coating liquid can be applied to the outer surface of the balloon 30 in a more appropriate quantity. In addition, the contact force in contact of the dispensing tube 134 with the balloon 30 can be easily set to a desirable value, so that, for example, the morphological form of the drug in the coating formed on the balloon 30 can be set more appropriately.

According to the balloon coating method as above, the position of the proximal portion of the core member 207 is coincident with the position of the proximal end of the balloon 30 or is on the proximal side of the balloon 30, and the proximal portion of the core member 207 does not protrude from the proximal opening portion 92. This makes it possible to dispose the core member 207 at a position where the balloon 30 is provided, while ensuring that the core member 207 does not protrude from the proximal opening portion 92 and the core member 207 is prevented from interfering with surrounding members or the like during rotation, whereby the rotation of the balloon 30 can be stabilized. Therefore, the coating liquid can be applied to the outer surface of the balloon 30 in a more appropriate quantity. The contact force in contact of the dispensing tube 134 with the balloon 30 can be easily set to a desirable value, so that, for example, the morphological form of the drug in the coating formed on the balloon 30 can be set more appropriately.

In the balloon coating method as above, the separated distance of the proximal portion of the core member 207 from the proximal opening portion 92 is up to 50 mm. This makes it possible to dispose the core member 207 over a wide as possible range of the guide wire lumen 91, while ensuring that the core member 207 does not protrude from the proximal opening portion 92 and the core member 207 is prevented from interfering with surrounding members or the like during rotation, whereby the rotation of the balloon 30 can be stabilized. Therefore, the coating liquid can be applied to the outer surface of the balloon 30 in a more appropriate quantity. In addition, the contact force by which the dispensing tube 134 contacts the balloon 30 can be easily set to a desirable value, so that, for example, the morphological form of the drug in the coating formed on the balloon 30 can be set more appropriately.

In the balloon coating method as above, the value obtained by subtracting the outside diameter of the core member 207 from the inside diameter of the guide wire lumen 91 is greater than 0 mm and not greater than 0.5 mm. Therefore, the diameter of the core member 207 is not too large in relation to the inside diameter of the guide wire lumen 91, so that damage to the inner tube 90, in which is formed the guide wire lumen 91, by the core member 207 can be restrained effectively. Further, since the diameter of the core member 207 is not too small in relation to the inside diameter of the guide wire lumen 91, deformation of the inner tube 90 can be effectively restrained from occurring when the inner tube 90 is clamped.

Further, the balloon coating method according to the first embodiment is a balloon coating method for forming a coating layer 2 containing a water-insoluble drug on an outer surface of a balloon 30 of a balloon catheter 10, wherein the method includes: fixing a distal joint portion 34 (connection portion) between an inner tube 90 penetrating the inside of the balloon 30 and the balloon 30 in such a manner as to clamp the distal joint portion 34 by at least two clamping portions 193 each having a groove-shaped curved surface extending along the axis X of the inner tube 90; and moving a dispensing tube 134 for supplying a coating liquid containing the drug relative to the balloon 30 in the axial direction X of the balloon 30, while rotating the balloon 30 about the axis of the balloon 30, to thereby apply the coating liquid to the outer surface of the balloon 30. According to the balloon coating method configured as above, since the distal joint portion 34 constituting a joint between the inner tube 90 and the balloon 30 is fixed in the manner of being clamped by the clamping portions 193 having the groove-shaped curved surfaces, the inner tube 90 and the region of inflation of the balloon 30 are prevented from being damaged, they can be inhibited from becoming eccentric, and the position of the outer surface of the balloon 30 becomes less liable to fluctuate during rotation. Therefore, the coating liquid can be applied to the outer surface of the balloon 30 in an appropriate quantity. In addition, since the position of the outer surface of the balloon 30 is less liable to fluctuate during rotation, the contact force in contact of the dispensing tube 134 with the balloon 30 can be easily set to a desirable value, so that, for example, the morphological form of the drug in the coating formed on the balloon 30 can be set appropriately.

In addition, according to the balloon coating method as above, in the application of the coating liquid, the coating liquid containing the drug is applied to the outer surface of the balloon 30 by rotating the balloon 30 while pulling the balloon 30 in the axial direction X of the balloon 30 by clamping portions 193. This ensures that bend of the balloon 30 is straightened by the tensile force, so that the position of the outer surface of the balloon 30 becomes less liable to fluctuate during rotation. Therefore, the coating liquid can be applied to the outer surface of the balloon 30 in an appropriate quantity. In addition, the contact force in contact of the dispensing tube 134 with the balloon 30 can be easily set to a desirable value, so that, for example, the morphological form of the drug in the coating formed on the balloon 30 can be set more appropriately. Although a grasping force by the clamping portions 193 is increased because of the exertion of the tensile force, damaging of the inner tube 90 and the balloon 30 can be restrained because the distal joint portion 34 is grasped by the clamping portions 193 having the groove-shaped curved surfaces.

In the balloon coating method as above, at least two clamping portions 193 are provided in a collet chuck 191. As a result, the distal joint portion 34 can be fixed by the collet chuck 191 easily and assuredly; further, a tensile force can be effectively exerted on the balloon 30.

Further, the balloon coating method according to the first embodiment is a balloon coating method for forming a coating layer 32 containing a water-insoluble drug on an outer surface of a balloon 30 of a balloon catheter 10, wherein the method includes applying the coating liquid containing the drug to the outer surface of the balloon 30 by moving a dispensing tube 134 for supplying the coating liquid relative to the balloon 30 in the axial direction X of the balloon 30, while rotating the balloon 30 about the axis X of the balloon 30 by applying rotating forces to the balloon catheter 10 on both the proximal side and the distal side of a region of inflation of the balloon 30 (a cylindrical portion 31 and tapered portions 33 on both sides thereof) and at the same rotational speed. In the balloon coating method configured as above, since the rotating forces are applied to the balloon catheter 10 on both the proximal side and the distal side of the region of inflation of the balloon 30 and at the same rotational speed, the balloon 30 becomes less liable to be twisted or to become eccentric. Therefore, the position of the outer surface of the balloon 30 becomes less liable to fluctuate during rotation, so that the coating liquid can be applied to the outer surface of the balloon 30 in an appropriate quantity. In addition, since the position of the outer surface of the balloon 30 becomes less liable to fluctuate during rotation, the contact force in contact of the dispensing tube 134 with the balloon 30 can be easily set to a desirable value, so that, for example, the morphological form of the drug in the coating formed on the balloon 30 can be set appropriately.

According to the balloon coating method as above, in the step of applying the coating liquid, the coating liquid is applied to the outer surface of the balloon 30 by rotating the balloon 30 while pulling the balloon 30 in the axial direction X of the balloon 30. As a result, bending of the balloon catheter 10 is straightened by the tensile force, so that rotating forces can be easily applied to the balloon catheter 10 from both the proximal portion and the distal portion of the balloon catheter 10.

In addition, according to the balloon coating method as above, in the application of the coating liquid, the distal joint portion 34 between the inner tube 90 penetrating the inside of the balloon 30 and the balloon 30 is clamped and pulled, whereby a tensile force is exerted in the axial direction X of the balloon 30. As a result, a rotating force can be effectively applied to the balloon catheter 10 through the distal joint portion 34, which is greater in thickness than the surrounding parts, has an outer circumferential surface composed of the flexible material of the balloon 30, and is therefore easy to clamp and apply a rotating force thereto.

According to the balloon coating method as above, in the step of applying the coating liquid, while the balloon 30 is being rotated about the axis X of the balloon 30, an end portion of the flexible dispensing tube 134 that is formed with an opening portion for ejecting the coating liquid contacts the outer surface of the balloon 30 in such a manner as to face in a direction reverse to the rotating direction of the balloon 30. In this condition, the dispensing tube 134 is moved relative to the balloon 30 in the axial direction X of the balloon 30, and, concurrently with this movement, the coating liquid is ejected from the opening portion, whereby the coating liquid is applied to the outer surface of the balloon 30. As a result, the dispensing tube 134 facing in the direction reverse to the rotating direction of the balloon 30 contacts the balloon 30, whereby a frictional force there is increased, resulting in a condition where the balloon 30 might be liable to be twisted or become eccentric. When rotating forces are applied to the balloon catheter 10 on both the proximal side and the distal side and at the same rotational speed, however, the possibility of the balloon 30 being twisted or becoming eccentric can be lowered. Accordingly, rotation of the balloon 30 can be stabilized, while promoting crystallization of the water-insoluble drug, by the dispensing tube 134 facing in the direction reverse to the rotating direction of the balloon 30. As a result, the contact force in contact of the dispensing tube 134 with the balloon 30 can be easily set to a desirable value, so that, for example, the morphological form of the drug in the coating formed on the balloon 30 can be set appropriately.

Further, the balloon coating method according to the first embodiment is a balloon coating method for forming a coating layer 32 containing a water-insoluble drug on an outer surface of an inflatable balloon 30 of a balloon catheter 10 having the balloon 30 at a distal portion of an elongate catheter shaft 20 (shaft), wherein the method includes: accommodating the catheter shaft 20 in a rectilinearly extending groove portion 182 of a support base 181 provided with the groove portion 182, closing the groove portion 182 with a lid portion 183, and supporting the catheter shaft 20 such that the catheter shaft 20 is rotatable within the groove portion 182; and moving a dispensing tube 134 for supplying a coating liquid containing the drug relative to the balloon 30 in the axial direction X of the balloon 30, while rotating the balloon 30 about the axis of the balloon 30, to thereby apply the coating liquid to the outer surface of the balloon 30. In the balloon coating method configured as above, since the catheter shaft 20 (shaft) of the balloon catheter 10 is rotated within the groove portion 182, bending of the catheter shaft 20 is straightened and an accurate rotary motion is promoted, so that the balloon 30 becomes less liable to be twisted or become eccentric. Therefore, the position of the outer surface of the balloon 30 becomes less liable to fluctuate during rotation, and the coating liquid can be applied to the outer surface of the balloon 30 in an appropriate quantity. In addition, since the position of the outer surface of the balloon 30 becomes less liable to fluctuate during rotation, the contact force in contact of the dispensing tube 134 with the balloon 30 can be easily set to a desirable value, so that, for example, the morphological form of the drug in the coating formed on the balloon 30 can be set appropriately. In addition, the catheter shaft 20 can be rotated while straightening its bend, by only accommodating the catheter shaft 20 in the groove portion 182 and closing the groove portion 182 with the lid portion 183, which ensures an easy operation.

In the balloon coating method as above, the groove portion 182 is located on an extension line of the driving shaft 111 for applying a rotating force to the hub 40 of the balloon catheter 10. This helps ensure that the axis of the driving shaft 111 and the axis of the catheter shaft 20 within the groove portion 182 coincide with each other, so that rotation of the balloon catheter 10 is stabilized, and the balloon 30 becomes less liable to be twisted or become eccentric.

In the balloon coating method as above, the groove portion 182 varies from part to part in at least one of width and depth. This enables those parts of the catheter shaft 20 which differ in shape or diameter to be disposed in those parts of the groove portion 182 which differ in width, so that rotation of the catheter shaft 20 can be stabilized, while restraining abrasion or damaging of the catheter shaft 20.

According to the balloon coating method as above, in the application of the coating liquid, the balloon 30 is rotated by applying rotating forces to the balloon catheter 10 on both the proximal side and the distal side and at the same rotational speed. As a result, even in a condition where the rotation might become unstable due to a frictional force generated due to the rotation within the groove portion 182, the balloon 30 becomes less liable to be twisted or become eccentric, since the rotating forces are applied to the balloon catheter 10 on both the proximal side and the distal side and at the same rotational speed. For this reason, the position of the outer surface of the balloon 30 becomes less liable to fluctuate during rotation, so that the coating liquid can be applied to the outer surface of the balloon 30 in an appropriate quantity. In addition, since the position of the outer surface of the balloon 30 becomes less liable to fluctuate during rotation, the contact force in contact of the dispensing tube 134 with the balloon 30 can be easily set to a desirable value, so that, for example, the morphological form of the drug in the coating formed on the balloon 30 can be set appropriately.

Because the coating liquid is ejected by putting the dispensing tube 134 into contact with the outer surface of the balloon 30 in such a manner that the ejection end 136 faces in the direction reverse to the rotating direction of the balloon 30, the water-insoluble drug in the coating layer 32 formed on the outer surface of the balloon 30 can be set into a morphological form wherein the crystals of the drug include a plurality of elongate bodies having independent long axes. In addition, in the balloon coating method as above, the coating liquid is ejected while the dispensing tube 134 is in contact with the outer surface of the balloon 30 in such a manner that the ejection end 136 faces in the direction reverse to the rotating direction of the balloon 30, whereby an appropriate contact is realized between the dispensing tube 134 and the balloon 30, and, for example, the morphological form and the size of the drug contained in the coating layer 32 can be set more freely.

<Second Embodiment>

Figure 11:
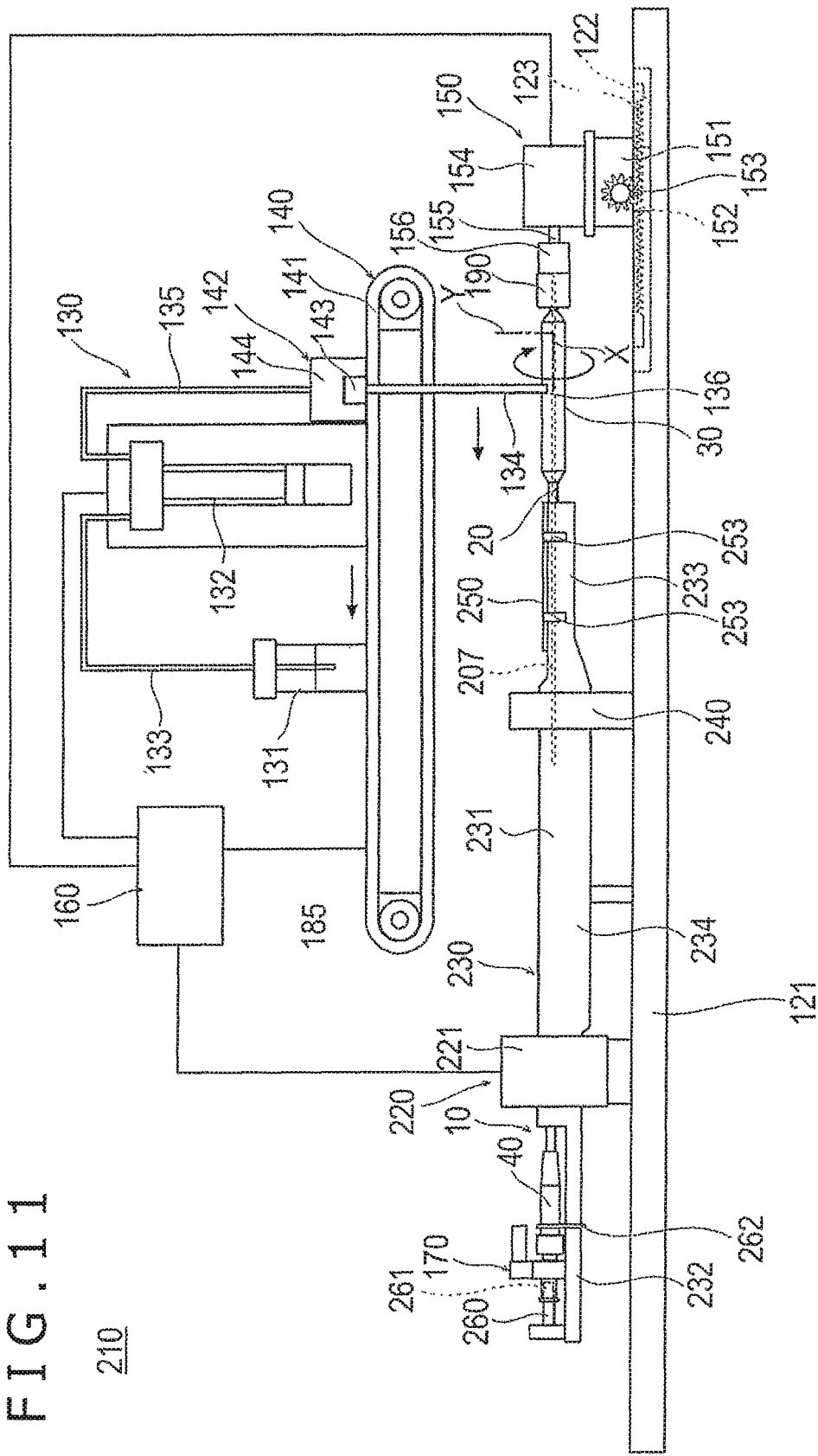
FIG. 11 is a schematic view showing an apparatus configured to carry out a balloon coating method according to a second embodiment of the present disclosure.
Figure 12:
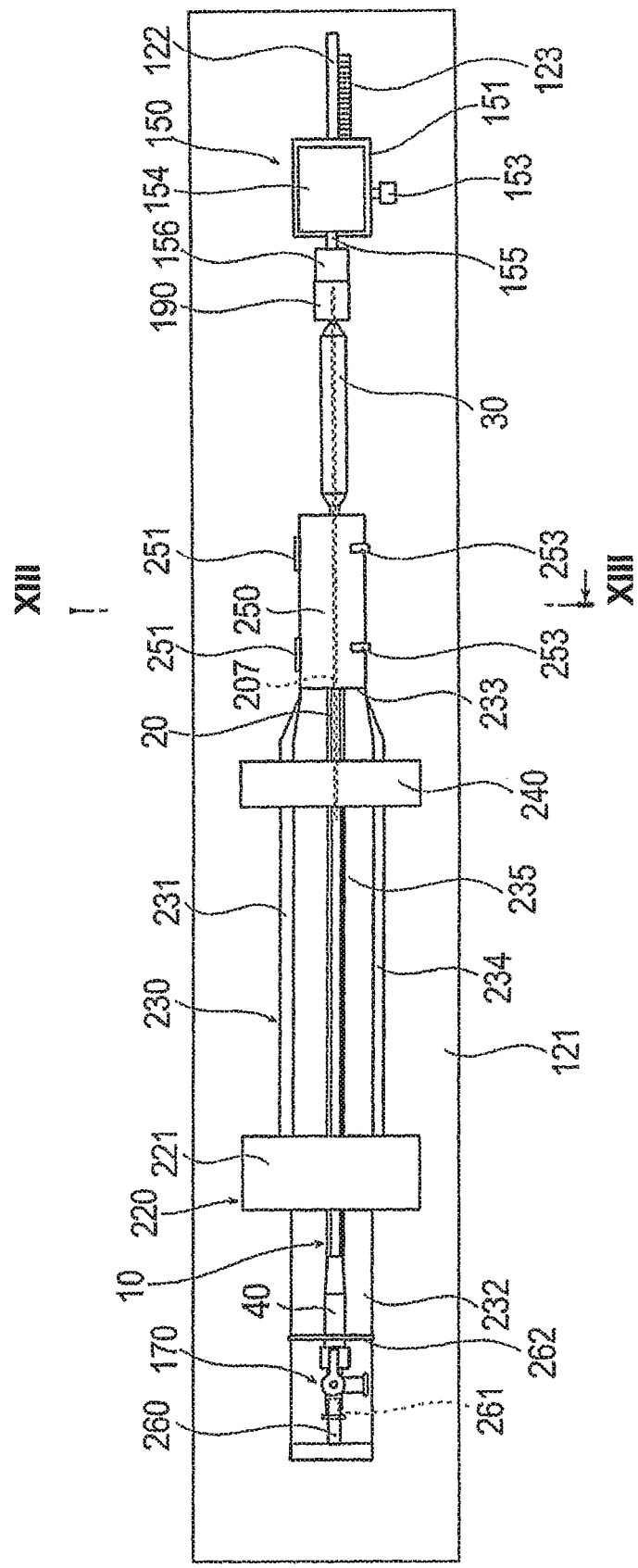
FIG. 12 is a plan view, as viewed from above, of the apparatus configured to carry out the balloon coating method according to the second embodiment.
Figure 13:
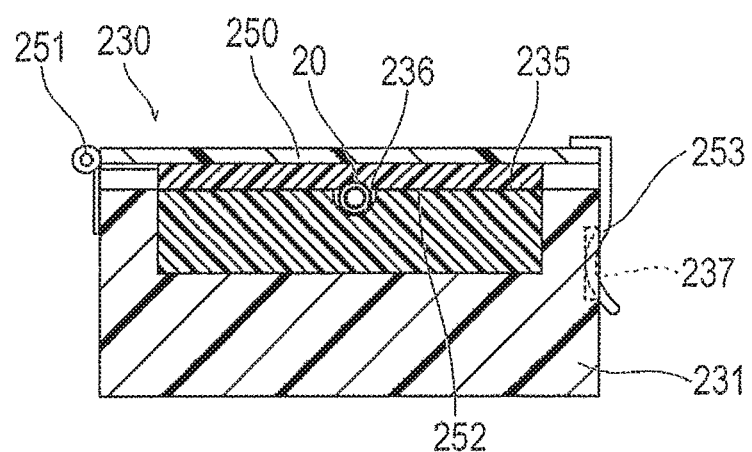
FIG. 13 is a cross-sectional view taken along line XIII-XIII of FIG. 12.
Figure 14:
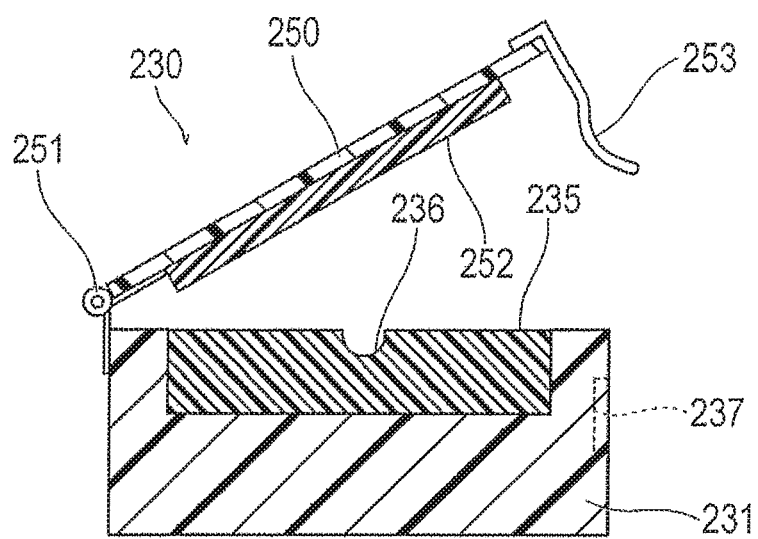
FIG. 14 is a cross-sectional view showing a state where a lid portion is opened.

A balloon coating method according to a second embodiment of the present disclosure includes rotating a balloon catheter 10 while holding the balloon catheter 10 on a support part rotatable together with the balloon catheter 10, thereby to form a coating layer 32 containing a water-insoluble drug on a surface of a balloon 30. The balloon coating method according to the second embodiment is carried out by a balloon coating apparatus 210 shown in FIGS. 11 and 12. The parts of the apparatus having the same or equivalent functions to those in the first embodiment are denoted by the same reference symbols as used above, and a detailed description of these parts is not repeated.

The balloon coating apparatus 210 includes a rotation driving section 220 (first rotation driving section) configured to apply a rotating force to the balloon catheter 10, a support part 230 configured to support the balloon catheter 10, and a bearing section 240 configured to support the support part 230 such that the support part 230 can be rotated. Further, the balloon coating apparatus 210 includes a bed 121, a coating section 130 provided with a dispensing tube 134, a rectilinear moving section 140 configured to move the dispensing tube 134, a tension section 150 (second rotation driving section), and a control unit 160 configured to control the balloon coating apparatus 210.

The rotation driving section 220 includes a first motor 221 which is fixed to the bed 121 and holds the support part 230 such that the support part 230 can be rotated.

The support part 230 penetrates the first motor 221 and is supported to be rotatable by the first motor 221. The support part 230 includes a support base 231 for holding the balloon catheter 10, and a lid portion 250 configured to clamp the balloon catheter 10 together with the support base 231. Further, the support part 230 includes hinge portions 251 configured to interlock the lid portion 250 such that the lid portion 250 can be opened and closed relative to the bed 121, and a support shaft 260 inserted in a three-way cock 170 attached to the balloon catheter 10.

The support base 231 includes a support base proximal portion 232 penetrating the first motor 221, a support base distal portion 233 to which the lid portion 250 is interlocked, and a support base central portion 234 formed between the support base proximal portion 232 and the support base distal portion 233.

The support base proximal portion 232 is a part configured to support a proximal portion of the balloon catheter 10, and penetrates the first motor 221, with the support shaft 260 being fixed on the proximal side of the first motor 221. The support shaft 260 is inserted in the three-way cock 170 attached to the balloon catheter 10, and fixes a proximal portion of the balloon catheter 10. With the three-way cock 170 attached to a hub 40, an inflation fluid can flow into the balloon 30 to inflate the balloon 30, by opening the three-way cock 170, and the inflated state of the balloon 30 can be maintained, by closing the three-way cock 170.

The support base distal portion 233 is a part configured to support a distal portion of the catheter shaft 20, and is located on the distal side of the bearing section 240, with the lid portion 250 turnably interlocked by the hinge portions 251. The support base distal portion 233 has a support surface 235 formed of a flexible material for clamping the catheter shaft 20 between itself and the lid portion 250. The support surface 235 is formed with a groove portion 236 in which part of the catheter shaft 20 is accommodated such that the catheter shaft 20 can be clamped at an appropriate position. The lid portion 250 has a pressing surface 252 formed of a flexible material for clamping the catheter shaft 20 between itself and the support surface 235. The support surface 235 and the pressing surface 252 are elastically deformed by clamping the catheter shaft 20 therebetween, and hold the catheter shaft 20 by elastic forces. Examples of the material or materials constituting the support surface 235 and the pressing surface 252 include expanded polyurethane and expanded polyethylene. The side surface of the support base distal portion 233 includes a recess 237 configured to interlock with a locking mechanism 253 provided on the lid portion 250 for fixing the lid portion 250 to the support base distal portion 233. The locking mechanism 253 is, for example, snap fit.

The support base central portion 234 is formed with the support surface 235 for supporting the catheter shaft 20, penetrates the bearing section 240, and is rotatably supported by the bearing section 240.

The width and depth of the groove portion 236 are preferably smaller than the outside diameter of the catheter shaft 20 by approximately 0.5 mm to 3.5 mm, such that the catheter shaft 20 can be clamped between the groove portion 236 and the lid portion 250.

The shape of the groove portion 236 in a section orthogonal to the X-direction has a semicircular bottom surface in this embodiment, this is not restrictive; for example, the shape may be a V shape or a tetragonal shape. The shape of the groove portion 236 is preferably such a shape as to make surface contact with the catheter shaft 20, such that the catheter shaft 20 is not liable to be damaged. Therefore, the shape of the groove portion 236 preferably does not have a projecting part, such as a W-shaped part, in section orthogonal to the X-direction. The groove portion 236 need not be provided.

The lid portion 250 is turnably held on the support base distal portion 233 by the hinge portions 251, can cover the support surface 235 to close the groove portion 236, and can be separated from the support surface 235 to expose the groove portion 236. The lid portion 250 is formed with the pressing surface 252 for clamping the catheter shaft 20 against the support surface 235.

The balloon catheter 10 has a core member 207 disposed within a guide wire lumen 91. The core member 207 has its distal portion protruding distally beyond a distal opening portion 93 of the guide wire lumen 91, and has its proximal portion located on the proximal side of a position of being clamped by the support surface 235 and the pressing surface 252. The length of protrusion of the core member 207 from the distal opening portion 93 is not particularly limited. For restraining the balloon catheter 10 from being crushed when clamped by a collet chuck 191, however, the protrusion length is preferably such a length as to be able to protrude assuredly, and is, for example, 2 mm to 50 mm.

Since the distal portion of the core member 207 protrudes distally beyond the distal opening portion 93 of the guide wire lumen 91 and the proximal portion of the core member 207 is located on the proximal side of the balloon 30, the core member 207 is present on the inside of the part to be clamped by the clamping portions 193, whereby the balloon catheter 10 can be restrained from deformation due to crushing.

Since the proximal portion of the core member 207 is located on the proximal side of the position of being clamped by the support base 231 having the support surface 235 and the lid portion 250 having the pressing surface 252, the core member 207 is present on the inside of the part to be clamped by the support surface 235 and the pressing surface 252, so that the balloon catheter 10 is restrained from deformation due to crushing.

The distal portion of the support shaft 260 is formed with a male luer taper 261 where its diameter decreases distally. The male luer taper 261, by being inserted into a female luer taper 171 formed in the three-way cock 170, can be fitted to the female luer taper 171 by a frictional force. The taper ratio of the male luer taper 261 and the female luer taper 171 is prescribed in ISO 594 and JIS (commentary on standards and reference concerning medical devices), and is prescribed to be 6%. The range of insertion of the support shaft 260 is within the range of the three-way cock 170. Therefore, the support shaft 260 can be fitted to and detached from the three-way cock 170 easily, which ensures enhanced usability.

The male luer taper 261 of the support shaft 260 may be inserted into and fitted to the female luer taper 171 formed at a hub proximal opening portion 41 of the hub 40, instead of the three-way cock 170. The support shaft 260 is not inserted distally beyond the hub 40. This permits the support shaft 260 to be fitted to and detached from the hub 40 easily, which ensures enhanced usability.

The control unit 160 is composed, for example, of a computer, and generally controls the rotation driving section 220, the rectilinear moving section 140, the tension section 150 and the coating section 130. The control unit 160 can cause the first motor 221 of the rotation driving section 220 and the second motor 154 of the tension section 150 to rotate synchronously at the same rotational speed. In addition, the control unit 160 can generally control the rotational speed of the balloon 30, initial positioning of the dispensing tube 134 relative to the balloon 30, the moving speed of the dispensing tube 134 in the axial direction X relative to the balloon 30, the ejection rate of the drug from the dispensing tube 134, and the like.

Now, a balloon coating method for forming a coating layer 32 containing a water-insoluble drug on a surface of a balloon 30 by use of the balloon coating apparatus 210 will be described below.

First, the three-way cock 170 is interlocked to the hub proximal opening portion 41 of the hub 40 of the balloon catheter 10, the three-way cock 170 is opened, and an inflation fluid is introduced into the balloon 30 by use of a syringe or the like to inflate the balloon 30, after which the three-way cock 170 is closed, to thereby maintain the inflated state of the balloon 30. The coating layer 32 can also be formed on the surface of the balloon 30 without inflating the balloon 30, and, in that case, it is unnecessary to supply an inflation fluid into the balloon 30.

Next, the lid portion 250 interlocked to the support base 231 is opened, the catheter shaft 20 is accommodated in the groove portion 236, and the lid portion 250 is closed, such as to maintain a closed state by the locking mechanism 253. As a result, the catheter shaft 20 is clamped and fixed between the support surface 235 and the pressing surface 252, while the support surface 235 and the pressing surface 252 which can be elastically deformed are deformed flexibly. In this instance, deformation of the catheter shaft 20 can be restrained, since the core member 207 is inserted over the range of that part of the catheter shaft 20 which is clamped between the support surface 235 and the pressing surface 252.

Next, the male luer taper 261 of the support shaft 260 is inserted into and interlocked to the female luer taper 171 of the three-way cock 170. By this, the hub 40 can be stably held by the support base 231 during rotation. In addition, the catheter shaft 20 can also be fixed to the support base proximal portion 232 by a linear member 262, such as rubber band or wire.

Subsequently, a distal joint portion 34 of the balloon catheter 10 is clamped by the clamping portions 193 of the collet chuck 191. As a result, a rotating force can be applied to a distal portion of the balloon catheter 10 from the second motor 154.

The order in which the balloon catheter 10 is disposed on the support shaft 260, the collet chuck 191 and the support base 231 is not particularly restricted.

Next, a dial 153 is rotated to move the second motor 154 and the collet chuck 191 distally, whereon a tensile force acts on the balloon catheter 10, whereby bending of the balloon 30 is straightened. In this instance, since the catheter shaft 20 is clamped between the support surface 235 and the pressing surface 252, the tensile force does not act on the proximal side of the part being clamped.

Subsequently, a driving portion 144 is operated, to position the dispensing tube 134 relative to the balloon 30. The dispensing tube 134 is brought closer to an outer surface of the balloon 30, and is bent by being pressed against the balloon 30 when making contact with the balloon 30. In this instance, a side surface on an end portion side of the dispensing tube 134 is configured to contact the outer surface of the balloon 30, by appropriately disposing the relevant components.

Next, a coating liquid is supplied to the dispensing tube 134 while controlling the liquid feed quantity by a liquid feed pump 132, and the balloon catheter 10 is rotated together with the support base 231 by the first motor 221 and the second motor 154. Then, a movable base 141 is moved, to gradually move the dispensing tube 134 proximally along the X-direction. Since the dispensing tube 134 is moved relative to the balloon 30, the coating liquid ejected from an ejection end 136 of the dispensing tube 134 is applied to the outer surface of the balloon 30 while drawing a spiral. That is, the coating liquid is applied to the outer surface of the balloon 30 in a spiral manner.

Since the balloon catheter 10 is clamped between the pressing surface 252 and the support surface 235, the part on the proximal side of the position of the part being clamped does not influence the rotation of the balloon 30. Therefore, stable rotation of the balloon 30 can be realized without strict restriction of bend, eccentricity or the like on the proximal side of the position where the balloon catheter 10 is clamped between the pressing surface 252 and the support surface 235. Consequently, unevenness of the thickness of the coating liquid applied can be restrained, and it becomes easy to control the thickness and morphological form of the coating layer 32.

Thereafter, the solvent contained in the coating liquid applied to the surface of the balloon 30 is volatilized, resulting in the formation of the coating layer 32 containing the water-insoluble drug on the surface of the balloon 30.

Since the extending direction of the dispensing tube 134 toward the ejection end 136 (the ejection direction) is reverse to the rotating direction of the balloon 30, the water-insoluble drug in the coating layer 32 formed on the outer surface of the balloon 30 is formed to include a morphological form wherein the crystals include a plurality of elongate bodies having independent long axes.

The drug in the coating formed on the outer surface of the balloon 30 can assume different morphological forms such as crystalline form, amorphous form and mixed forms thereof. Even where the drug assumes a crystalline form, there exist various morphological forms which differ in crystal structure. Further, crystals and amorphous phases may be disposed regularly in the coating layer 32, or may be disposed irregularly in the coating layer 32.

By moving the dispensing tube 134 gradually in the axial direction X while rotating the balloon 30, the coating layer 32 is formed on the outer surface of the balloon 30 gradually along the axial direction X. After the range of the part to be coated of the balloon 30 is entirely coated with the coating layer 32, the rotation driving section 220, the rectilinear moving section 140, the tension section 150 and the coating section 130 are stopped.

Thereafter, the balloon catheter 10 is dismounted from the balloon coating apparatus 210, and the coating of the balloon 30 is completed.

As aforementioned, the balloon coating method according to the second embodiment is a balloon coating method for forming a coating layer 32 containing a water-insoluble drug on an outer surface of an inflatable balloon 30 of a balloon catheter 10 having the balloon 30 provided at a distal portion of an elongate catheter shaft 20 (shaft), wherein the method includes: holding the catheter shaft 20 on a support part 230 rotatable about the axis X of the balloon 30; and moving a dispensing tube 134 for supplying the coating liquid containing the drug relative to the balloon 30 in the axial direction X of the balloon 30, while rotating the balloon 30 together with a support base 231, thereby to apply the coating liquid to the outer surface of the balloon 30.

In the balloon coating method configured as above, the balloon 30 is rotated in a state wherein the catheter shaft 20 is held on the rotatable support part 230; therefore, bending of the catheter shaft 20 and the like are not liable to influence the rotation of the balloon 30, so that the balloon 30 is not liable to be twisted or become eccentric. For this reason, the position of the outer surface of the balloon 30 is not liable to fluctuate during rotation, so that the coating liquid can be applied to the outer surface of the balloon 30 in an appropriate quantity. In addition, since the position of the outer surface of the balloon 30 is not liable to fluctuate during rotation, the contact force in contact of the dispensing tube 134 with the balloon 30 can be easily set to a desirable value, so that, for example, the morphological form of the drug in the coating formed on the balloon 30 can be set appropriately.

According to the balloon coating method as above, the support part 230 includes the support base 231 formed with the rectilinear groove portion 236 capable of accommodating at least part of the catheter shaft 20 (shaft), and the lid portion 250 capable of covering the lid portion 236, and, during the holding of the catheter shaft 20, the catheter shaft 20 is accommodated in the groove portion 236 and the groove portion 236 is covered with the lid portion 250, to thereby hold the catheter shaft 20 on the support part 230. As a result, the catheter shaft 20 can be held easily and assuredly in such a manner as not to slip off from the groove portion 236.

According to the balloon coating method as above, during the holding of the catheter shaft 20, the catheter shaft 20 is clamped by the support base 231 and the lid portion 250. Therefore, the catheter shaft 20 can be firmly held on the support part 230, rotation of the balloon 30 is stabilized, and the balloon 30 becomes less liable to be twisted or become eccentric.

According to the balloon coating method as above, during the holding of the catheter shaft 20, the catheter shaft 20 is held by the support part 230, with the core member 207 inserted in the catheter shaft 20. This ensures that even when the catheter shaft 20 is held by the support part 230, deformation of the catheter shaft 20 can be restrained.

According to the balloon coating method as above, while applying the coating liquid, the balloon catheter 10 is rotatably supported by the bearing section 240, which is provided on the distal side of the rotation driving section 220 for applying a rotating force to the support part 230, while rotating the balloon catheter 10 by the rotation driving section 220. This results in that the rotation of the support part 230, which extends distally from the rotation driving section 220, is stabilized. Therefore, the rotation of the balloon 30 is stabilized, so that the balloon 30 becomes less liable to be twisted or get eccentric.

The present disclosure is not limited only to the aforementioned embodiments, and various modifications can be made by those skilled in the art within the scope of the technical thought of the present disclosure. For example, while the coating liquid is applied to the balloon 30 from the distal side toward the proximal side of the balloon 30 in the aforementioned first and second embodiments, the coating liquid may be applied from the proximal side toward the distal side.

In addition, while the dispensing tube 134 extends downward along the vertical direction to contact the balloon 30 in the aforementioned first and second embodiments, the extending direction of the dispensing tube 134 is not specifically restricted. For instance, the extending direction may be inclined against the vertical direction, or the dispensing tube 134 may extend sideways or upward.

While the balloon catheter 10 whose balloon 30 is to be coated is a rapid exchange type balloon catheter in the balloon coating methods according to the aforementioned embodiments, a balloon of an over-the-wire type balloon catheter having a guide wire lumen from a hub to a distal portion may be coated.

Figure 15:
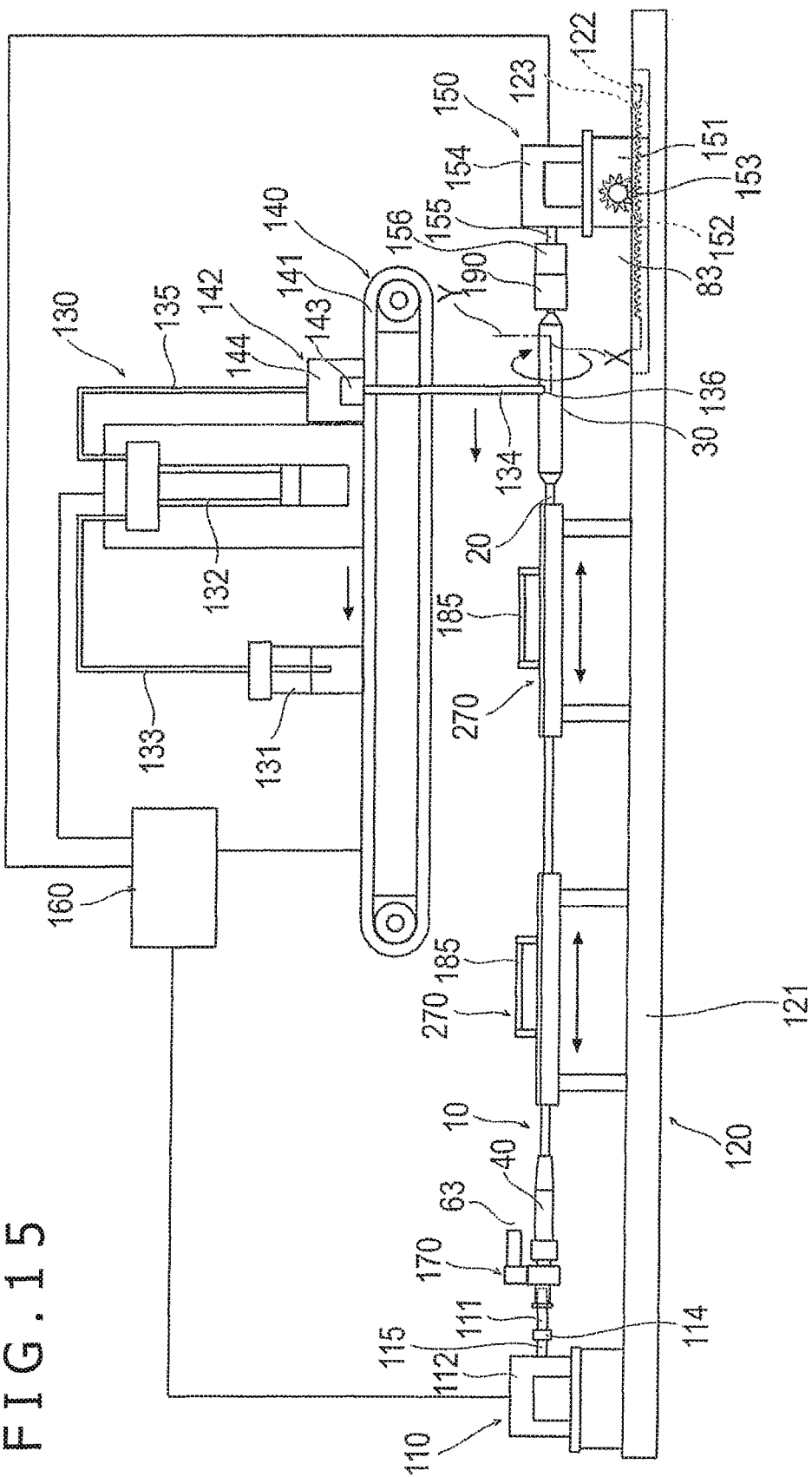
FIG. 15 is a schematic view showing a modification of the balloon coating apparatus in the first embodiment.

Further, as in a modification of the first embodiment that is illustrated in FIG. 15, there may be provided a plurality of (in the example shown in FIG. 15, two) support parts 270 by which the catheter shaft 20 is rotatably supported. The support parts 270 may be arbitrarily movable along the axis X of the balloon 30, or along the extending direction of groove portions (not shown) provided in the support parts 270. The plurality of support parts 270 are aligned along the extending direction of the groove portions (not shown) provided in the support parts 270.

With the catheter shaft 20 thus supported by the plurality of support parts 270, the rotation of the elongate catheter shaft 20 can be stabilized, while reducing the friction between each support part 270 and the catheter shaft 20 and thereby restraining abrasion or damaging of the catheter shaft 20.

In addition, since the support parts 270 are movable, the support parts 270 can be moved prior to the step of supporting the catheter shaft 20 by the support parts 270. As a result, the catheter shaft 20 can be supported at desirable positions, whereby rotation of the balloon catheter 10 can be stabilized.

Each support base may be provided with a plurality of lid portions.

Having described several embodiments of the present disclosure which represent examples of the balloon coating method and balloon rotating method disclosed here, it is to be understood that the disclosure is not limited to those precise embodiments and that various changes and modifications could be effected therein by those skilled in the art without departing from the spirit or scope of the disclosure as defined in the appended claims. It is expressly intended that all such changes, modifications and equivalents which fall within the scope of the claims are embraced by the claims.

What is claimed is:

1. A balloon coating method for forming a coating layer containing a water-insoluble drug on an outer surface of a balloon of a balloon catheter, the balloon catheter including an elongate shaft possessing a distal portion at which is provided the balloon which is inflatable and which possesses an axis, the shaft possessing an outer surface, the balloon coating method comprising:

positioning the shaft on a rotatable support part so that the outer surface of the shaft faces the rotatable support part, the balloon projecting distally beyond a distal end of the support part and being held by a clamp; and moving a dispensing tube relative to the balloon in an axial direction of the balloon while rotating the balloon together with the support part about the axis of the balloon and while also dispensing the coating liquid containing the water-insoluble drug from the dispensing tube to coat the outer surface of the balloon with the coating liquid, the balloon and the support part being rotated by a motor that is proximal of the balloon, a part of the shaft that is supported on the rotatable support part being located closer to the balloon than the motor.

2. The balloon coating method according to claim 1, wherein the rotatable support part includes a support base provided with a rectilinear groove, the rotatable support part also including a lid mounted on the support base and movable between an open position and a closed position, and the positioning of the shaft comprises positioning the shaft in the groove, and further comprising moving the lid from the closed position to the open position so that the lid covers the groove and the shaft, and so that the shaft is held between the support base and the lid, the rotating of the balloon together with the support part comprising rotating the support base after the lid is moved to the closed position.

3. The balloon coating method according to claim 2, further comprising clamping the shaft between the support base and the lid.

4. The balloon coating method according to claim 1, wherein the positioning of the shaft comprises positioning the shaft on the support part while a core member is positioned inside the shaft.

5. The balloon coating method according to claim 1, wherein the rotating of the balloon comprises rotating the balloon catheter while the balloon catheter is rotatably supported by a bearing section provided on a distal side of a rotation driving section configured to apply a rotating force to the support part, while rotating the balloon catheter by the rotation driving section.

6. The balloon coating method according to claim 1, wherein the support part includes a groove and the positioning of the shaft comprises positioning the shaft in the groove.

7. The balloon coating method according to claim 1, wherein a portion of the support part is rotatably supported on a bearing section, and the rotating of the balloon comprises rotating the balloon catheter by the motor which is located proximal of the bearing section.

8. A balloon rotating method for rotating a balloon catheter that includes an inflatable balloon at a distal portion of an elongate shaft, the shaft possessing an outer surface, the balloon rotating method comprising:
    positioning the shaft on a support part that is rotatable about an axis of the balloon so that the outer surface of the shaft faces the rotatable support part, the balloon projecting distally beyond a distal end of the support part and being held by a clamp; and
    rotating the balloon together with the support part about the axis, the balloon and the support part being rotated by a motor that is proximal of the balloon, a part of the support part on which the shaft is positioned and that is rotated by the motor being located distal of a distal-most end of the motor.

9. The balloon rotating method according to claim 8, wherein
    the rotatable support part includes a support base provided with a rectilinear groove, the rotatable support part also including a lid mounted on the support base and movable between an open position and a closed position, and
    the positioning of the shaft comprises positioning the shaft in the groove of the support base, and further comprising moving the lid from the open position to the closed position so that the lid covers the groove and the shaft, and so that the shaft is held between the support base and the lid, the rotating of the balloon together with the support part comprising rotating the support base after the lid is moved to the closed position.

10. The balloon rotating method according to claim 9, further comprising the shaft between the support base and the lid.

11. The balloon rotating method according to claim 8, wherein the positioning of the shaft comprises positioning the shaft on the support part while a core member is positioned in a lumen in the shaft.

12. The balloon rotating method according to claim 8, wherein the coating rotating of the balloon comprises rotating the balloon catheter while the balloon catheter is rotatably supported by a bearing section provided on a distal side of a rotation driving section configured to apply a rotating force to the support part, while rotating the balloon catheter by the rotation driving section.

13. The balloon coating method according to claim 1, wherein the support part includes a support base provided with a groove, the positioning of the shaft on the rotatable support part includes positioning the shaft in the groove on the support base, and the rotating of the support part about the axis of the balloon comprising rotating the support base while the shaft is positioned in the groove of the support base.

14. The balloon coating method according to claim 1, wherein the rotating of the support base occurs while the shaft is positioned in a groove of the support base.

15. The balloon coating method according to claim 8, wherein the support part includes a support base provided with a groove, the positioning of the shaft on the rotatable support part includes positioning the shaft in the groove on the support base, and the rotating of the support part about the axis of the balloon comprising rotating the support base while the shaft is positioned in the groove of the support base.

16. The balloon coating method according to claim 8, wherein the rotating of the support base occurs while the shaft is positioned in a groove of the support base.

17. A balloon coating method for forming a coating layer on an outer surface of a balloon of a balloon catheter, the balloon catheter including an elongate shaft possessing a distal portion at which is provided the balloon which is inflatable and which possesses an axis, the shaft possessing an outer surface, the balloon coating method comprising:
    positioning the shaft on a rotatable support part so that the outer surface of the shaft faces the rotatable support part, the balloon projecting distally beyond a distal end of the support part and being held by a clamp; and
    moving a dispensing tube relative to the balloon in an axial direction of the balloon while rotating the balloon together with the support part about the axis of the balloon and while also dispensing the coating liquid containing the water-insoluble drug from the dispensing tube to coat the outer surface of the balloon with the coating liquid, the shaft of the balloon catheter extending distally beyond a distal-most end of the motor and proximally beyond a proximal-most end of the motor.

18. The balloon coating method according to claim 17, wherein the support part on which the shaft is positioned and which is rotated by the operation of the motor includes a support base proximal portion penetrating the motor, a support base distal portion that is distal of the support base proximal portion, and a support base central portion positioned between the support base proximal portion and the support base distal portion, the support base central portion of the support part penetrating a bearing section and being rotatably supported by the bearing section.

19. The balloon coating method according to claim 17, wherein a portion of the support part that is rotated by the motor is rotatably supported by a bearing section positioned between the balloon and the motor, at least a part of the shaft that is supported by the rotatable support part being located closer to the bearing section than the motor.

20. The balloon coating method according to claim 17, wherein a portion of the support part that is rotated by the motor penetrates the motor and supports a proximal portion of the balloon catheter.

* * * * *